US010368840B2

(12) United States Patent
Arai et al.

(10) Patent No.: US 10,368,840 B2
(45) Date of Patent: Aug. 6, 2019

(54) ULTRASONIC APPARATUS

(71) Applicant: Seiko Epson Corporation, Tokyo (JP)

(72) Inventors: Yoshio Arai, Shiojiri (JP); Kazuki Yoshida, Fujimi (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 16/052,729

(22) Filed: Aug. 2, 2018

(65) Prior Publication Data

US 2019/0038256 A1    Feb. 7, 2019

(30) Foreign Application Priority Data

Aug. 3, 2017    (JP) ................................. 2017-150475

(51) Int. Cl.
*A61B 8/00* (2006.01)
(52) U.S. Cl.
CPC .......... *A61B 8/4494* (2013.01); *A61B 8/4427* (2013.01); *A61B 8/4488* (2013.01); *A61B 8/461* (2013.01); *A61B 8/467* (2013.01); *A61B 8/56* (2013.01)
(58) Field of Classification Search
None
See application file for complete search history.

(56) References Cited

U.S. PATENT DOCUMENTS

| 4,862,893 | A  | * | 9/1989 | Martinelli | ............ | A61B 8/0833 |
| | | | | | | 600/459 |
| 7,105,986 | B2 | * | 9/2006 | Wildes | ................... | A61B 8/546 |
| | | | | | | 310/327 |
| 2004/0073118 | A1 | * | 4/2004 | Peszynski | ................ | A61B 8/12 |
| | | | | | | 600/459 |
| 2006/0241467 | A1 | * | 10/2006 | Takeda | ..................... | G10K 9/18 |
| | | | | | | 600/459 |
| 2008/0116765 | A1 | * | 5/2008 | Sugiura | ................. | B06B 1/0629 |
| | | | | | | 310/334 |
| 2010/0179430 | A1 | | 7/2010 | Sano et al. | | |
| 2012/0157853 | A1 | | 6/2012 | Gelly et al. | | |
| 2013/0195333 | A1 | * | 8/2013 | Singh | .................... | G03F 7/0035 |
| | | | | | | 382/131 |
| 2015/0266058 | A1 | | 9/2015 | Yoshida et al. | | |

FOREIGN PATENT DOCUMENTS

| JP | 60-128795 | A | 7/1985 |
| JP | 05-199587 | A | 8/1993 |
| JP | 06-105844 | A | 4/1994 |
| JP | 3302069 | B2 | 7/2002 |
| JP | 3745703 | B2 | 2/2006 |

(Continued)

*Primary Examiner* — J. San Martin
(74) *Attorney, Agent, or Firm* — Harness, Dickey & Pierce, P.L.C.

(57) ABSTRACT

An ultrasonic apparatus includes an ultrasonic element substrate that includes an ultrasonic element array transmitting an ultrasonic wave in a first direction, and a first conductive film provided on the first direction side of the ultrasonic element array, a casing portion that has a conductive member provided to surround the ultrasonic element substrate on a side intersecting the first direction of the ultrasonic element substrate, and a support substrate that is provided on an opposite side to the first direction of the ultrasonic element substrate, supports the ultrasonic element substrate, and has conductivity.

15 Claims, 12 Drawing Sheets

(56) References Cited

FOREIGN PATENT DOCUMENTS

| | | |
|---|---|---|
| JP | 2007-181060 A | 7/2007 |
| JP | 4118737 B2 | 7/2008 |
| JP | 2012-135616 A | 7/2012 |
| JP | 5049340 B2 | 10/2012 |
| JP | 2015-185915 A | 10/2015 |

\* cited by examiner

ULTRASONIC APPARATUS

BACKGROUND

1. Technical Field

The present invention relates to an ultrasonic apparatus.

2. Related Art

An ultrasonic probe is a device which transmits an ultrasonic wave to a subject, and receives a reflected wave which is reflected at the inside or a surface of the subject. The ultrasonic probe is a transducer which converts the received reflected wave into an electric signal. The ultrasonic probe is a part forming an ultrasonic apparatus. The ultrasonic apparatus includes a calculation circuit, and the electric signal output from the ultrasonic probe is input to the calculation circuit. The calculation circuit calculates a cross-sectional image of the inside of the subject. The cross-sectional image is referred to as an ultrasonic image.

The ultrasonic probe includes an ultrasonic element array in which a plurality of ultrasonic elements are arranged. Each ultrasonic element transmits an ultrasonic wave, and receives a reflected wave. The ultrasonic element includes a capacitive micromachined ultrasonic transducer (CMUT) type ultrasonic element in which an electrode is provided on a vibration film, and a piezoelectric micromachined ultrasonic transducer (PMUT) type ultrasonic element employing a piezoelectric element. In the ultrasonic element array, the ultrasonic elements are arranged, and are connected to each other via wires. The wires connect the respective ultrasonic elements to each other so as to be long, and thus easily receive electromagnetic noise.

International Publication No. 2008/114582 discloses a CMUT type ultrasonic probe. According thereto, an ultrasonic element array transmits ultrasonic waves in a first direction. A conductive film is provided on the first direction side of the ultrasonic element array. A conductive film is also provided on a side of the ultrasonic element array orthogonal to the first direction. The conductive films are connected to a chassis ground of an ultrasonic apparatus. Consequently, it is possible to prevent noise from being applied to an electric signal output from the ultrasonic element array due to electromagnetic noise which advances toward the ultrasonic element array.

In the ultrasonic probe disclosed in International Publication No. 2008/114582, a conductive film is not provided on the ultrasonic element array on an opposite side to the first direction. Therefore, the influence of electromagnetic noise which advances toward the ultrasonic element array from the opposite side to the first direction cannot be prevented. Such electromagnetic noise causes the same problem not only in the ultrasonic probe but also in an ultrasonic apparatus which detects the presence or absence of an object to be measured or measures a distance or the like by using an ultrasonic wave. Therefore, an ultrasonic apparatus which can prevent the influence of electromagnetic noise advancing toward an ultrasonic element array is desirable.

SUMMARY

An advantage of some aspects of the invention is to solve at least a part of the problems described above, and the invention can be implemented as the following forms or application examples.

Application Example 1

An ultrasonic apparatus according to this application example includes an ultrasonic element substrate that includes an ultrasonic element array transmitting an ultrasonic wave in a first direction, and a first conductive film provided on the first direction side of the ultrasonic element array; a casing portion that has a conductive member provided to surround the ultrasonic element substrate on a side intersecting the first direction of the ultrasonic element substrate; and a support substrate that is provided on an opposite side to the first direction of the ultrasonic element substrate, supports the ultrasonic element substrate, and has conductivity.

According to this application example, the ultrasonic apparatus includes the ultrasonic element substrate, the casing portion, and the support substrate. The ultrasonic element substrate includes the ultrasonic element array and the first conductive film. The ultrasonic element array transmits an ultrasonic wave in the first direction. In the ultrasonic element array, ultrasonic elements are arranged and are connected to each other via wires. The wires connect the respective ultrasonic elements to each other so as to be long, and thus easily receive electromagnetic noise.

The first conductive film is provided on the first direction side of the ultrasonic element array. Electromagnetic noise directed toward the ultrasonic element array from the first direction side is reflected and blocked or is absorbed and attenuated by the first conductive film. The casing portion includes the conductive member, and the conductive member is provided to surround the ultrasonic element substrate on the side intersecting the first direction of the ultrasonic element substrate. Therefore, electromagnetic noise directed toward the ultrasonic element array from the direction side intersecting the first direction is reflected and blocked or is absorbed and attenuated by the conductive member.

The support substrate is provided on an opposite side to the first direction of the ultrasonic element substrate, and supports the ultrasonic element substrate. The support substrate is conductive. Therefore, electromagnetic noise which is directed toward the ultrasonic element array from the opposite direction side to the first direction is reflected and blocked or is absorbed and attenuated by the support substrate. Therefore, electromagnetic noise directed toward the ultrasonic element array from all directions is reflected and blocked or is absorbed and attenuated by the first conductive film, the conductive member, and the support substrate, and thus it is possible to reduce the electromagnetic noise directed toward the ultrasonic element array.

Application Example 2

In the ultrasonic apparatus according to the application example, a material of the casing portion is a resin, the conductive member is a thin film provided on a surface of the casing portion, a protective member is provided on the first direction side of the ultrasonic element substrate, a second conductive film is provided on a side of the protective member directed toward the ultrasonic element substrate, the first conductive film, the second conductive film, the conductive member, and the support substrate are electrically connected to each other, and the second conductive film is adhered to the conductive member via a conductive adhesive.

According to this application example, a material of the casing portion is a resin, and thus the casing portion is easily formed even if a shape thereof is complex compared with a case where a material thereof is metal. The conductive member is a thin film provided on the surface of the casing portion, and can thus be easily provided by using a film forming device such as a deposition device.

The protective member is provided on the first direction side of the ultrasonic element substrate. The protective member protects the ultrasonic element substrate. The protective member is provided with the second conductive film on the side directed toward the ultrasonic element substrate. The first conductive film, the second conductive film, the conductive member, and the support substrate are electrically connected to each other. Consequently, it is possible to reduce electromagnetic noise received by the ultrasonic element array. The second conductive film and the conductive member are adhered to each other via the conductive adhesive. Therefore, it is possible to easily perform fixation between the protective member and the casing portion and electrical connection between the second conductive film and the conductive member.

Application Example 3

In the ultrasonic apparatus according to the application example, the conductive member and the casing portion are integrally formed, and the first conductive film, the conductive member, and the support substrate are electrically connected to each other.

According to this application example, the conductive member and the casing portion are integrally formed. In other words, the casing portion is made of a conductive material. The first conductive film, the conductive member, and the support substrate are electrically connected to each other. In this configuration, the ultrasonic element array is surrounded by the conductive member, and thus it is possible to prevent electromagnetic noise from reaching the ultrasonic element array. Second processing for providing the conductive member in the casing portion can be omitted, and thus it is possible to manufacture the ultrasonic apparatus with high productivity.

Application Example 4

In the ultrasonic apparatus according to the application example, a material of the first conductive film is copper.

According to this application example, a material of the first conductive film is copper. The copper has low electrical resistance, and can thus absorb electromagnetic noise with high efficiency.

Application Example 5

In the ultrasonic apparatus according to the application example, the first conductive film is provided with a plurality of holes.

According to this application example, the first conductive film is provided with a plurality of holes. An ultrasonic wave transmitted from the ultrasonic element array passes through the plurality of holes, and thus attenuation thereof can be reduced. Therefore, the ultrasonic apparatus can transmit an ultrasonic wave with high efficiency.

Application Example 6

The ultrasonic apparatus according to the application example further includes a flat cable through which an electric signal is transmitted to the ultrasonic element array; and a braided shield that surrounds the flat cable, and the support substrate is connected to the braided shield.

According to this application example, the ultrasonic apparatus includes the flat cable and the braided shield. The plurality of ultrasonic elements are provided in the ultrasonic element array, and thus a plurality of wires for sending signals to the respective ultrasonic elements are necessary. The wires have the form of the flat cable, and thus have a thin structure. Therefore, the ultrasonic apparatus can be thinned more than in a case of using a cable in which wires are bundled in a rod shape. The braided shield is provided to surround the flat cable. The support substrate is connected to the braided shield. Therefore, the braided shield is also connected to the support substrate, and thus it is possible to prevent electromagnetic noise from reaching the flat cable.

Application Example 7

An ultrasonic apparatus according to this application example includes an ultrasonic element substrate that is provided with an ultrasonic element array transmitting an ultrasonic wave in a first direction; and an electric wave shield portion that is located in the first direction of the ultrasonic element array, a direction intersecting the first direction, and a direction opposite to the first direction.

According to this application example, the ultrasonic apparatus includes the ultrasonic element substrate and the electric wave shield portion. The ultrasonic element substrate is provided with the ultrasonic element array. The ultrasonic element array transmits an ultrasonic wave. In the ultrasonic element array, the ultrasonic elements are arranged, and are connected to each other via wires. The wires connect the respective ultrasonic elements to each other so as to be long, and thus easily receive electromagnetic noise.

The electric wave shield portion is located in the first direction of the ultrasonic element array, the direction intersecting the first direction, and the direction opposite to the first direction. As mentioned above, the electric wave shield portion is provided to surround the ultrasonic element array. Therefore, electromagnetic noise directed toward the ultrasonic element array from all directions is reflected and blocked or is absorbed and attenuated by the electric wave shield portion. As a result, electromagnetic noise directed toward the ultrasonic element array can be prevented from reaching the ultrasonic element array.

Application Example 8

An ultrasonic apparatus according to this application example includes an ultrasonic element substrate that includes an ultrasonic element array transmitting an ultrasonic wave in a first direction, and a first conductive film provided on the first direction side of the ultrasonic element array; and a casing portion that has a conductive member provided to surround the ultrasonic element substrate on a side intersecting the first direction and an opposite side to the first direction of the ultrasonic element substrate.

According to this application example, the ultrasonic apparatus includes the ultrasonic element substrate and the casing portion. The ultrasonic element array and the first conductive film are provided on the ultrasonic element substrate. The ultrasonic element array transmits an ultrasonic wave in the first direction. In the ultrasonic element array, ultrasonic elements are arranged and are connected to each other via wires. The wires connect the respective ultrasonic elements to each other so as to be long, and thus easily receive electromagnetic noise.

The first conductive film is provided on the first direction side of the ultrasonic element array. Electromagnetic noise directed toward the ultrasonic element array from the first direction side is reflected and blocked or is absorbed and attenuated by the first conductive film. The casing portion includes the conductive member, and the conductive member is provided to on the side intersecting the first direction and the opposite side to the first direction of the ultrasonic element substrate. Therefore, electromagnetic noise directed toward the ultrasonic element array from the direction side intersecting the first direction and the opposite side to the first direction is reflected and blocked or is absorbed and attenuated by the conductive member. Therefore, electromagnetic noise directed toward the ultrasonic element array from all directions is reflected and blocked or is absorbed and attenuated by the first conductive film and the conductive member, and thus it is possible to prevent the electromagnetic noise from reaching the ultrasonic element array.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments will be described with reference to the drawings. Each member in each drawing is illustrated in a differing scale so as to have a recognizable size on each drawing.

First Embodiment

Figure 1:
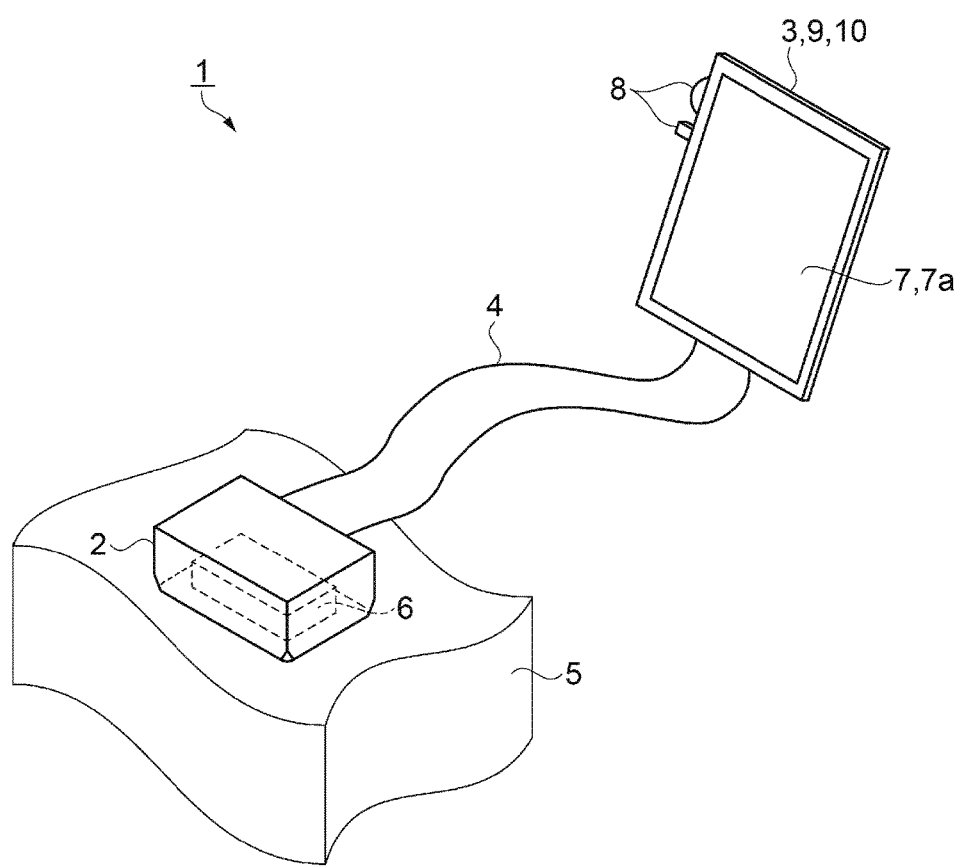
FIG. 1 is a schematic perspective view illustrating a configuration of an ultrasonic apparatus according to a first embodiment.

An ultrasonic apparatus according to the present embodiment will be described with reference to FIGS. 1 to 8. FIG. 1 is a schematic perspective view illustrating a configuration of an ultrasonic apparatus. As illustrated in FIG. 1, an ultrasonic apparatus 1 includes an ultrasonic probe 2 and a main body portion 3. The ultrasonic probe 2 and the main body portion 3 are provided separately from each other, and are electrically connected to each other via a flat cable 4.

The ultrasonic probe 2 transmits an ultrasonic wave to a subject 5. The ultrasonic probe 2 receives a reflected wave which is a reflected at the inside or a surface of the subject 5, and converts the reflected wave into an electric signal. Next, the ultrasonic probe 2 transmits the electric signal including information regarding the reflected wave to the main body portion 3 via the flat cable 4.

The ultrasonic probe 2 includes an ultrasonic element array 6 therein. Ultrasonic elements are arranged and provided on the ultrasonic element array 6. Each ultrasonic element transmits an ultrasonic wave to the subject 5. Apart at which an ultrasonic wave is easily reflected and a part through which an ultrasonic wave easily passes are present inside the subject 5. An ultrasonic wave advances through the subject 5, and is reflected when reaching the part at which the ultrasonic wave is easily reflected. Some of ultrasonic waves transmitted toward the subject 5 are reflected at the inside of the subject 5, change their advancing directions, and advance toward the ultrasonic element array 6. The ultrasonic element is a transducer which converts a variation in sound pressure of the ultrasonic wave into voltage amplitude. The ultrasonic element array 6 receives a reflected wave of the ultrasonic wave, and converts the reflected wave into an electric signal.

The main body portion 3 has a rectangular tabular shape. The main body portion 3 has a size sufficient to be grasped with a single hand. The main body portion 3 includes a display device 7, an input device 8, a calculation device 9, and the like. The main body portion 3 includes a tabular main body casing portion 10, and the calculation device 9 is stored in the main body casing portion 10. Parts of the display device 7 and the input device 8 are exposed from the main body casing portion 10. A material of the main body casing portion 10 is metal, and is conductive. Therefore, the main body casing portion 10 functions as a chassis ground or an electromagnetic shield of the calculation device 9.

The input device 8 is formed of a rotation switch or a push switch. An operator operates the input device 8 so as to input various instructions to the ultrasonic apparatus 1. The calculation device 9 receives an electric signal output from the ultrasonic probe 2 so as to generate an ultrasonic image. The calculation device 9 outputs data of the ultrasonic image to the display device 7.

The display device 7 displays information such as an ultrasonic image. As the display device 7, a liquid crystal display, an organic electroluminescence display, a plasma display, or a surface electric field display may be used. A touch panel 7a is provided on a surface of the display device 7. The touch panel 7a is a transparent sheet-like switch provided on the surface of the display device 7. In a case where the operator touches the surface of the display device 7 with the finger, the touch panel 7a detects a position touched with the finger. The operator operates the touch panel 7a so as to input an instruction to the main body portion 3.

Figure 2:
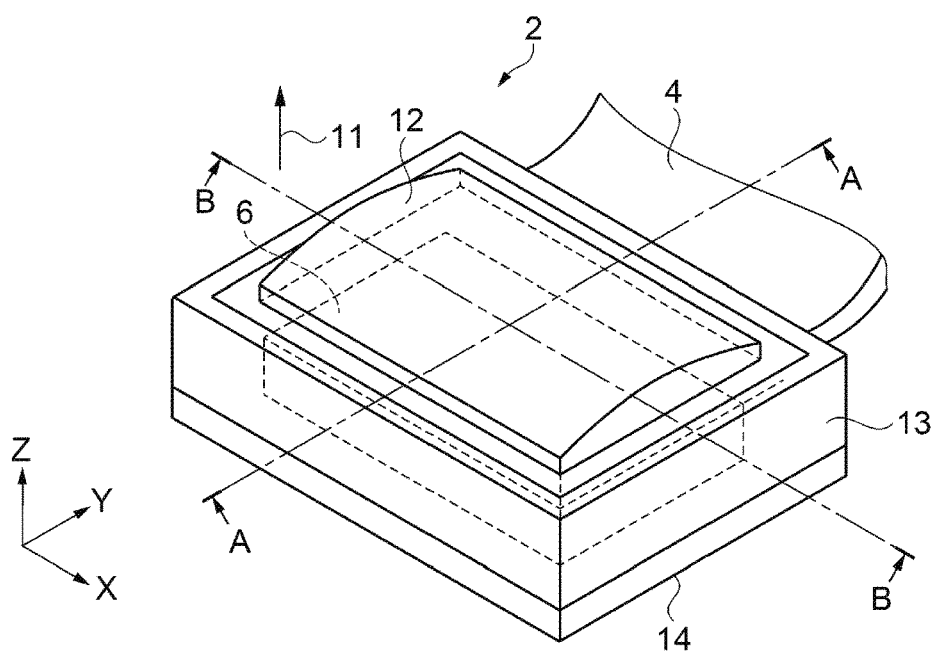
FIG. 2 is a schematic perspective view illustrating a configuration of an ultrasonic probe.

FIG. 2 is a schematic perspective view illustrating a configuration of the ultrasonic probe. As illustrated in FIG. 2, a shape of the ultrasonic probe 2 is a substantially tabular shape of a rectangular parallelepiped. A thickness direction of the ultrasonic probe 2 is set to a Z direction. A longitudinal direction of the ultrasonic probe 2 is set to an X direction in a plane direction orthogonal to the Z direction, and a direction orthogonal to the X direction is set to a Y direction.

In the Z direction, an upper direction in the drawing is a first direction 11 in which the ultrasonic probe 2 transmits an ultrasonic wave. The ultrasonic probe 2 is provided with an acoustic lens 12 as a protective member on a surface thereof on the first direction 11 side. The acoustic lens 12 is a columnar lens obtained by cutting a cylinder of which an axis extends in the X direction, along the axis. Therefore, the acoustic lens 12 has a convex lens shape when viewed from the X direction side. The acoustic lens 12 collects ultrasonic waves transmitted from the ultrasonic element array 6.

A casing portion 13 is provided on an outer circumference of the acoustic lens 12 and a side surface of the acoustic lens 12. The flat cable 4 is connected to the casing portion 13 on the +Y direction side. A support substrate 14 is provided on a surface of the ultrasonic probe 2 on the −Z direction side. The support substrate 14 supports the ultrasonic element array 6. The ultrasonic probe 2 is thin, and thus has a shape easily fixed to the subject 5 with a tape or the like.

Figure 3:
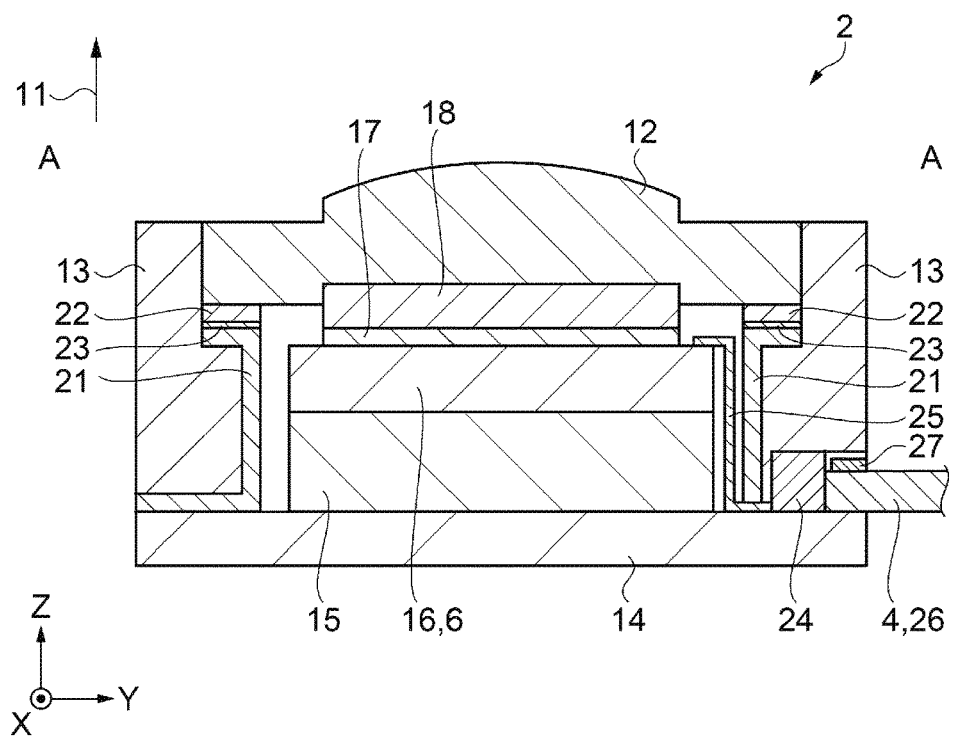
FIG. 3 is a schematic side sectional view illustrating a structure of the ultrasonic probe.
Figure 4:
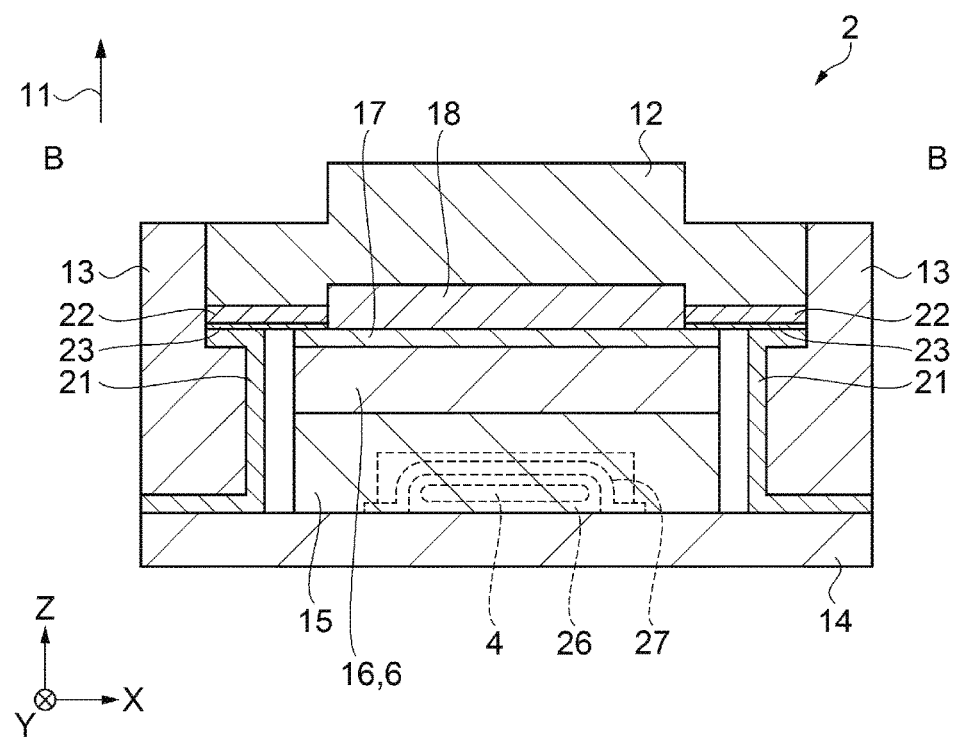
FIG. 4 is a schematic side sectional view illustrating a structure of the ultrasonic probe.

FIGS. 3 and 4 are schematic side sectional views illustrating a structure of the ultrasonic probe. FIG. 3 is a view in which a section along the line A-A in FIG. 2 is viewed from the +X direction side. FIG. 4 is a view in which a section along the line B-B in FIG. 2 is viewed from the −Y direction side. As illustrated in FIGS. 3 and 4, an ultrasonic wave absorption plate 15, an ultrasonic element substrate 16, a first conductive film 17, an acoustic matching portion 18, and the acoustic lens 12 are provided to overlap each other in this order on the support substrate 14.

The support substrate 14 is provided on an opposite side to the first direction 11 of the ultrasonic element substrate 16, and supports the ultrasonic element substrate 16 and the ultrasonic wave absorption plate 15. The support substrate 14 is conductive. Therefore, electromagnetic noise which is directed toward the ultrasonic element substrate 16 from the opposite direction side to the first direction 11 is reflected and blocked or is absorbed and attenuated by the support substrate 14. A material of the support substrate 14 may have strength and conductivity, and may employ various kinds of metals. In the present embodiment, for example, a copper alloy is used for the support substrate 14.

The ultrasonic wave absorption plate 15 absorbs an ultrasonic wave which is transmitted by the ultrasonic element substrate 16 in the opposite side to the first direction 11. The ultrasonic wave absorption plate 15 suppresses advancing of an ultrasonic wave which is directed toward the ultrasonic element substrate 16 from the opposite side to the first direction 11. A material of the ultrasonic wave absorption plate 15 is not particularly limited as long as the material absorbs an ultrasonic wave, and may employ silicon or the like. In the present embodiment, for example, a silicon substrate is used.

The ultrasonic element substrate 16 is a substrate on which the ultrasonic element array 6 is provided. Ultrasonic elements are arranged in a matrix form in the ultrasonic element array 6. The ultrasonic element array 6 receives an electric signal, and converts the electric signal into an ultrasonic wave. The ultrasonic element array 6 transmits an ultrasonic wave in the first direction 11. The ultrasonic element array 6 receives a reflected wave of the ultrasonic wave reflected at the inside of the subject 5, and converts the reflected wave into an electric signal.

The ultrasonic element substrate 16 includes the first conductive film 17, and the first conductive film 17 is provided on the first direction 11 side of the ultrasonic element array 6. The first conductive film 17 is a conductor, and hardly transmits an electric wave therethrough by absorbing the electric wave. Therefore, electromagnetic noise directed toward the ultrasonic element array 6 from the first direction 11 side is reflected and blocked or is absorbed and attenuated by the first conductive film 17, and thus it is possible to prevent the ultrasonic element array 6 from being exposed to the electromagnetic noise.

The acoustic lens 12 is provided on the first conductive film 17 via the acoustic matching portion 18. The acoustic matching portion 18 adjusts acoustic impedance between the ultrasonic element substrate 16 and the acoustic lens 12. The acoustic lens 12 and the acoustic matching portion 18 are made of a silicon resin mixed with whisker. The acoustic matching portion 18 is a layer adjusting acoustic impedance, and acoustic impedance of the acoustic matching portion 18 is adjusted between acoustic impedance of the ultrasonic element substrate 16 and acoustic impedance of the acoustic lens 12.

The casing portion 13 is provided around the ultrasonic wave absorption plate 15, the ultrasonic element substrate 16, the first conductive film 17, the acoustic matching portion 18, and the acoustic lens 12. The casing portion 13 includes a conductive member 21 inside thereof. The conductive member 21 is provided to surround the ultrasonic element substrate 16 on a side intersecting the first direction 11 of the ultrasonic element substrate 16. The conductive member 21 is provided over the whole periphery of the ultrasonic element substrate 16. Electromagnetic noise directed toward the ultrasonic element array 6 from the direction side intersecting the first direction 11 is reflected and blocked or is absorbed and attenuated by the conductive member 21. Therefore, it is possible to prevent electromagnetic noise from reaching the ultrasonic element array.

A material of the conductive member 21 is preferably conductive, and more preferably has low electrical resistance. A material of the conductive member 21 is not particularly limited, but may employ metal or the like. In the present embodiment, for example, copper or a copper alloy is used as a material of the conductive member 21. The copper has low electrical resistance, and can thus absorb electromagnetic noise with high efficiency.

The first conductive film 17 is provided in the ultrasonic element array 6 on the first direction 11 side. Electromagnetic noise directed toward the ultrasonic element array 6 from the first direction 11 side is reflected and blocked or is absorbed and attenuated by the first conductive film 17. The casing portion 13 includes the conductive member 21, and the conductive member 21 is provided to surround the ultrasonic element substrate 16 on the side intersecting the first direction 11 of the ultrasonic element substrate 16. Therefore, electromagnetic noise directed toward the ultrasonic element array 6 from the direction side intersecting the first direction 11 is reflected and blocked or is absorbed and attenuated by the conductive member 21.

The support substrate 14 is provided on an opposite side to the first direction 11 of the ultrasonic element substrate 16, and supports the ultrasonic element substrate 16. The support substrate 14 is conductive. Therefore, electromagnetic noise which is directed toward the ultrasonic element array 6 from the opposite direction side to the first direction 11 is reflected and blocked or is absorbed and attenuated by the support substrate 14. Therefore, electromagnetic noise directed toward the ultrasonic element array 6 from all directions is reflected and blocked or is absorbed and attenuated by the first conductive film 17, the conductive member 21, and the support substrate 14, and thus it is possible to prevent the electromagnetic noise from reaching the ultrasonic element array 6.

A material of the casing portion 13 is not particularly limited as long as the material has strength for maintaining a structure thereof, but, in the present embodiment, for example, a resin is used. The conductive member 21 is a thin film, and is provided on the surface of the casing portion 13. As a method of providing the conductive member 21 on the casing portion 13, a deposition method, a sputtering method, a chemical vapor deposition (CVD) method, or an electroless plating method may be used. As mentioned above, a material of the casing portion 13 is a resin, and thus the casing portion 13 is easily formed even if a shape thereof is complex compared with a case where a material thereof is metal. The conductive member 21 is a thin film provided on the surface of the casing portion 13, and can thus be easily provided by using a film forming device such as a deposition device.

The acoustic lens 12 is provided on the first direction 11 side of the ultrasonic element substrate 16. The acoustic lens 12 protects the ultrasonic element substrate 16. The acoustic lens 12 has a function of collecting ultrasonic waves. The acoustic lens 12 is provided with a second conductive film 22 on the ultrasonic element substrate 16 side. The second conductive film 22 is provided around the acoustic matching portion 18. The first conductive film 17 and the second conductive film 22 are disposed to overlap each other on the +X direction side and the −X direction side of the acoustic matching portion 18. The first conductive film 17 and the second conductive film 22 are adhered to each other via a conductive adhesive 23. The second conductive film 22 and the conductive member 21 are disposed to overlap each other around the acoustic matching portion 18. The second conductive film 22 and the conductive member 21 are adhered to each other via the conductive adhesive 23. Therefore, it is possible to easily perform fixation between the acoustic lens 12 and the casing portion 13 and electrical connection between the second conductive film 22 and the conductive member 21.

The conductive member 21 is also provided on a surface of the casing portion 13 on the support substrate 14 side. The casing portion 13 is fixed to the support substrate 14 such that the conductive member 21 is in contact with the support substrate 14. A fixation structure between the casing portion 13 and the support substrate 14 is not particularly limited. The fixation may be performed by using screws, and may be performed by using a clamp mechanism. The casing portion 13 and the support substrate 14 may be adhered to each other by using the conductive adhesive 23. With this configuration, the first conductive film 17, the second conductive film 22, the conductive member 21, and the support substrate 14 are electrically connected to each other.

A connector 24 is provided on the support substrate 14 on the +Y direction side. The connector 24 is interposed between the support substrate 14 and the casing portion 13. The ultrasonic element array 6 provided on the ultrasonic element substrate 16 is electrically connected to the connector 24 via a flexible printed wiring board 25. A plurality of wires are provided side by side on the flexible printed wiring board 25. Consequently, different electric signals can be transmitted to a plurality of ultrasonic elements via the flexible printed wiring board 25.

One end of the flat cable 4 is provided at the connector 24. The flat cable 4 includes a plurality of wires, and each wire is a thin coaxial cable. The connector 24 electrically connects the wires of the flexible printed wiring board 25 to the wires of the flat cable 4. The other end of the flat cable 4 is provided at the main body portion 3. The flat cable 4 transmits an electric signal to the ultrasonic element array 6 via the flexible printed wiring board 25. The plurality of ultrasonic elements are provided in the ultrasonic element array 6, and thus a plurality of wires for sending signals to the respective ultrasonic elements are necessary. The wires have the form of the flat cable 4, and thus have a thin structure. Therefore, the ultrasonic probe 2 can be thinned more than in a case of using a cable in which wires are bundled in a rod shape.

A braided shield 26 is disposed on an outer periphery of the flat cable 4, and the braided shield 26 surrounds the flat cable 4. The braided shield 26 is connected to the metallic main body casing portion 10 of the main body portion 3. The flat cable 4 surrounded by the braided shield 26 is fixed to the support substrate 14 via a wiring fixation portion 27. The braided shield 26 is sandwiched between the support substrate 14 and the wiring fixation portion 27. Therefore, the braided shield 26 is electrically connected to the support substrate 14. Thus, the support substrate 14 is electrically connected to the braided shield 26. The braided shield 26 is connected to the support substrate 14, and thus it is possible to prevent electromagnetic noise from entering the flat cable 4.

The support substrate 14 is electrically connected to the conductive member 21, the second conductive film 22, and the first conductive film 17. Therefore, the first conductive film 17, the second conductive film 22, the conductive member 21, and the support substrate 14 are electrically connected to each other. Consequently, electromagnetic noise received by the ultrasonic element array 6 is absorbed by the first conductive film 17, the second conductive film 22, the conductive member 21, and the support substrate 14, and thus it is possible to prevent the electromagnetic noise from reaching the ultrasonic element array 6.

Figure 5:
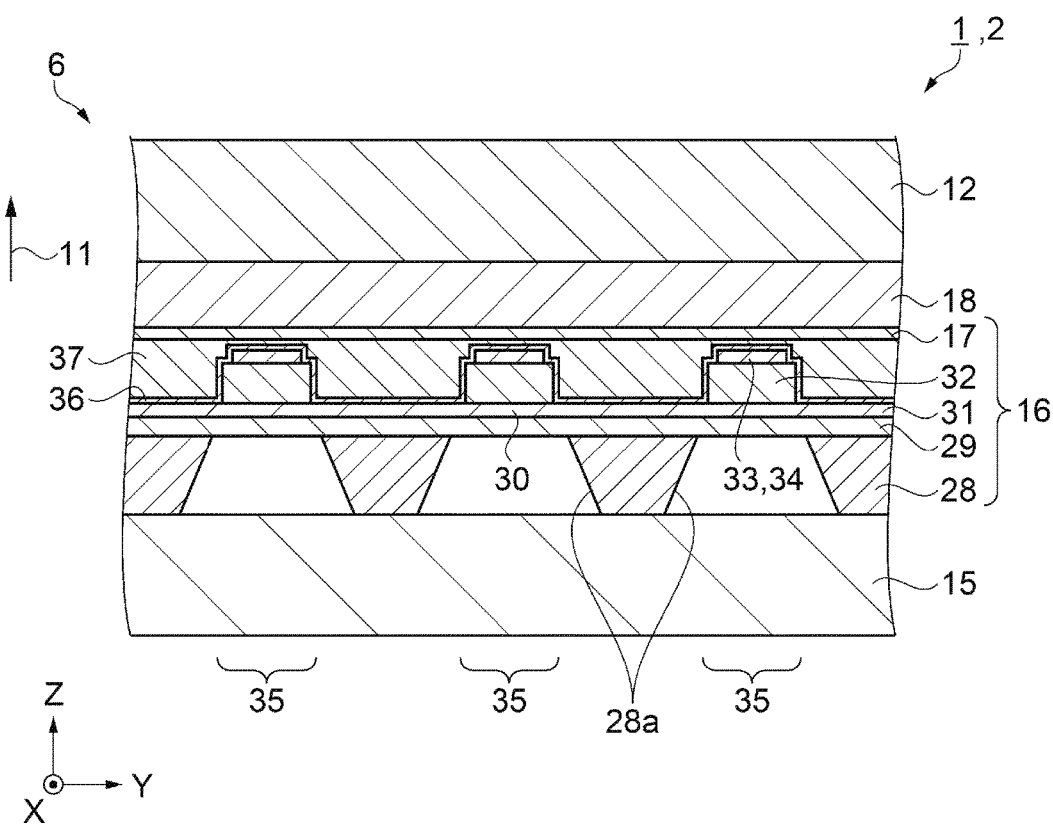
FIG. 5 is a schematic side sectional view for explaining a sectional structure of an ultrasonic element array.

FIG. 5 is a schematic side sectional view for explaining a sectional structure of the ultrasonic element array. As illustrated in FIG. 5, the ultrasonic element substrate 16 is provided to overlap the ultrasonic wave absorption plate 15. The ultrasonic element substrate 16 includes a base substrate 28, and the base substrate 28 is located on the ultrasonic wave absorption plate 15 side in the ultrasonic element substrate 16. Openings 28a are provided at the same interval in the base substrate 28. For example, silicon may be used as a material of the base substrate 28. The openings 28a are formed by etching a silicon substrate.

A vibration film 29 is provided on the base substrate 28 on the +Z direction side. The vibration film 29 is formed of a two-layer structure such as a $SiO_2$ layer and a $ZrO_2$ layer. The vibration film 29 is also referred to as a membrane. First electrodes 30 are provided on the vibration film 29. The first electrodes 30 are connected to each other via a first wire 31 extending in the Y direction. Piezoelectric layers 32 are provided on the first electrodes 30. Second electrodes 33 are provided on the piezoelectric layers 32. The second electrodes 33 are connected to each other via a second wire 34 extending in the X direction.

An ultrasonic element 35 is formed by the vibration film 29, the first electrode 30, the piezoelectric layer 32, and the second electrode 33. Ultrasonic elements 35 are arranged in a matrix form in the ultrasonic element array 6. The first electrodes 30, the first wire 31, the second electrodes 33, and the second wire 34 are metal films, and, in the present embodiment, for example, aluminum is used.

For example, lead zirconate titanate (PZT), lead titanate ($PbTiO_3$), lead zirconate ($PbZrO_3$), and lead lanthanum titanate ((Pb, La) $TiO_3$) may be used for the piezoelectric layer 32. In the present embodiment, for example, PZT is used for the piezoelectric layer 32.

When a voltage is applied between the first electrode 30 and the second electrode 33, the piezoelectric layer 32 expands and contracts in an in-surface direction. Therefore, if a voltage is applied to the piezoelectric layer 32, the piezoelectric layer 32 protrudes toward the opening 28a side, and thus the vibration film 29 is bent. An AC voltage is applied to the piezoelectric layer 32 such that the vibration film 29 vibrates in the film thickness direction, and thus an ultrasonic wave is transmitted in the first direction 11 due to vibration of the vibration film 29. A drive voltage applied to the piezoelectric layer 32 is, for example, 10 to 30 V in terms of peak-to-peak voltage, and a frequency is, for example, 1 to 10 MHz.

The ultrasonic element 35 also operates as a reception element receiving a reflected wave of an ultrasonic wave which is transmitted to and reflected at a target object and returns. The vibration film 29 vibrates due to the reflected wave of the ultrasonic wave, stress is applied to the piezoelectric layer 32 due to the vibration, and thus a voltage is generated between the first electrode 30 and the second electrode 33. The voltage may be extracted as a received signal.

An insulating film 36 is provided to cover the first wire 31, the piezoelectric layers 32, the second electrodes 33, and the second wire 34. The insulating film 36 is made of a material such as alumina. An internal acoustic matching portion 37 is provided to cover the insulating film 36. The internal acoustic matching portion 37 and the acoustic matching portion 18 have a function of alleviating mismatching of acoustic impedance between the ultrasonic element 35 and the acoustic lens 12. A silicon resin is used for the internal acoustic matching portion 37 and the acoustic matching portion 18.

Specifically, a silicon-based adhesive is used for the internal acoustic matching portion 37 and the acoustic matching portion 18. In the internal acoustic matching portion 37, the adhesive is cured such that the insulating film 36 is adhered to the first conductive film 17, and the cured adhesive functions as the internal acoustic matching portion 37. In the acoustic matching portion 18, the adhesive is cured such that the first conductive film 17 is adhered to the acoustic lens 12, and the cured adhesive functions as the acoustic matching portion 18.

The first conductive film 17 is provided on the internal acoustic matching portion 37 on the first direction 11 side. A material of the first conductive film 17 is not particularly limited as long as the material is conductive, but, in the present embodiment, is copper. The copper has low electrical resistance, and can thus absorb electromagnetic noise with high efficiency. The base substrate 28 to the first conductive film 17 are included in the ultrasonic element substrate 16. Therefore, the ultrasonic element substrate 16 includes the ultrasonic element array 6 and the first conductive film 17.

The acoustic matching portion 18 is provided on the first direction 11 side of the first conductive film 17. The acoustic matching portion 18 has a function of alleviating mismatching of acoustic impedance between the ultrasonic element 35 and the acoustic lens 12 along with the internal acoustic matching portion 37. The acoustic lens 12 is provided on the first direction 11 side of the acoustic matching portion 18. The acoustic lens 12 collects ultrasonic waves transmitted from the ultrasonic element array 6 at a predetermined location. The acoustic lens 12 protects the ultrasonic element array 6 so as to prevent the ultrasonic element array 6 from being dirty.

Figure 6:
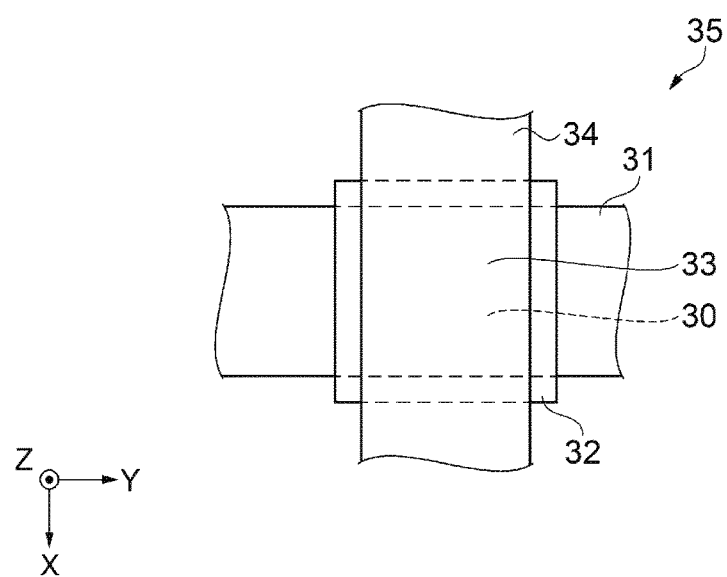
FIG. 6 is a schematic plan view illustrating a structure of an ultrasonic element.

FIG. 6 is a schematic plan view illustrating a structure of the ultrasonic element. As illustrated in FIG. 6, the second wire 34 is provided on the +Z direction side of the square piezoelectric layer 32. The second wire 34 extends in the X direction. The first wire 31 is provided on the −Z direction side of the piezoelectric layer 32. The first wire 31 extends in the Y direction. The first wire 31 in a region in which the first wire 31 intersects the second wire 34 when viewed from the first direction 11 is the first electrode 30. The second wire 34 in a region in which the first wire 31 intersects the second wire 34 when viewed from the first direction 11 is the second electrode 33.

Therefore, the first electrode 30 and the first wire 31 are an integrally formed conductive film. The second electrode 33 and the second wire 34 are an integrally formed conductive film. The first electrode 30 and the second electrode 33 are disposed to oppose each other with the piezoelectric layer 32 interposed therebetween.

Figure 7:
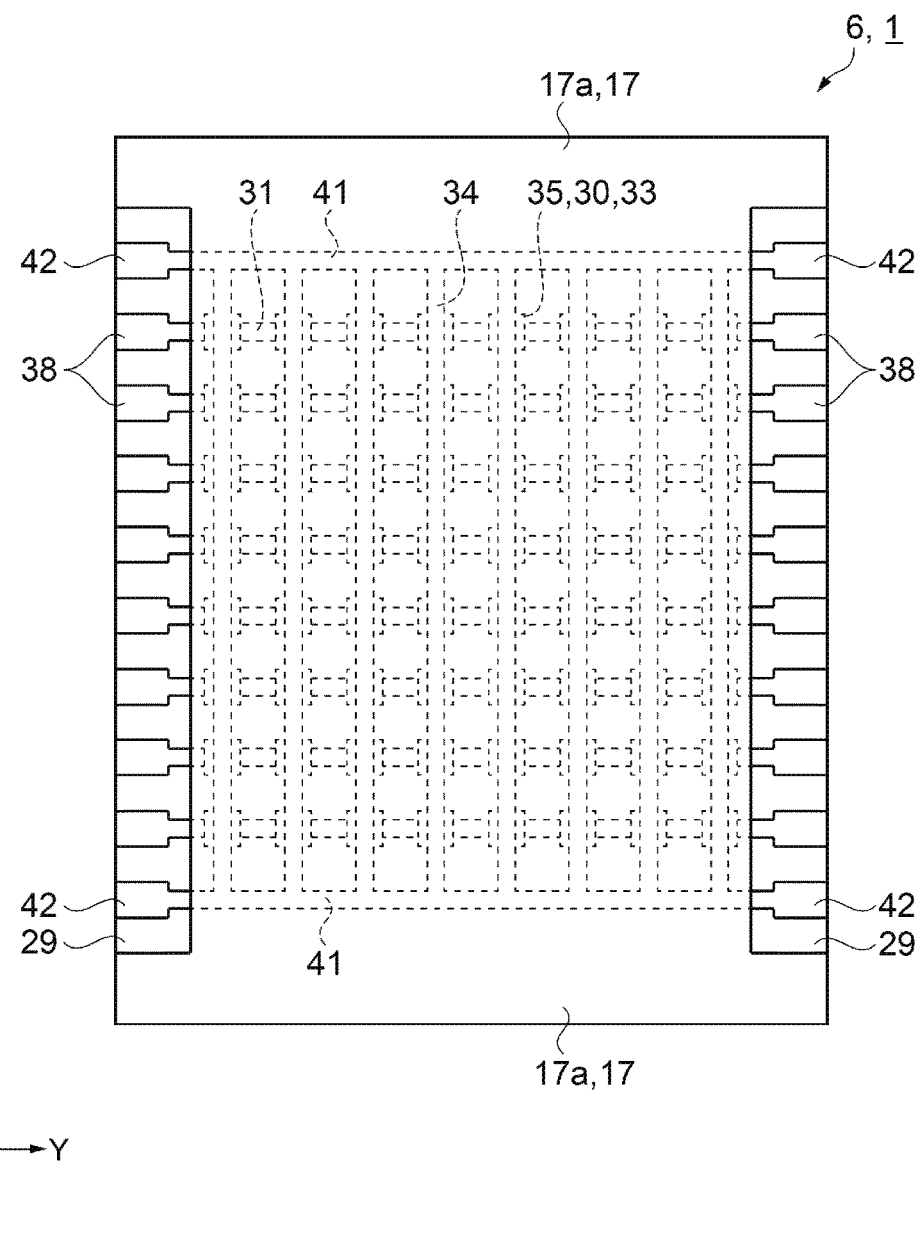
FIG. 7 is a schematic plan view illustrating a structure of the ultrasonic element array.

FIG. 7 is a schematic plan view illustrating a structure of the ultrasonic element array, and is a view in which the ultrasonic element substrate 16 is viewed from the first direction 11. As illustrated in FIG. 7, the ultrasonic elements 35 are arranged in a matrix form in the ultrasonic element array 6.

The first wire 31 connects the eight first electrodes 30 arranged in the Y direction to each other, and extends in the Y direction. First terminals 38 are provided at both ends of the first wire 31. Eight first wires 31 are provided, and thus eight first terminals 38 are also provided on one side. The second wire 34 connects the eight second electrodes 33 arranged in the X direction to each other, and extends in the X direction. Both ends of the second wire 34 are connected to second sub-wires 41 extending in the Y direction. Eight second wires 34 are provided, and the second wires 34 are all connected to the second sub-wires 41. Second terminals 42 are provided at both ends of each of the second sub-wires 41. Two second sub-wires 41 are provided, and thus two second terminals 42 are also provided on one side.

The first terminals 38 and the second terminals 42 are not covered with the insulating film 36, the internal acoustic matching portion 37, and the first conductive film 17, and are exposed. The first terminals 38 and the second terminals 42 are connected to the flexible printed wiring board 25. All of the second electrodes 33 are connected to the second terminals 42, and thus all of the second electrodes 33 have the same potential. The first electrodes 30 are connected to the first terminals 38 which are different from each other for the respective rows and are arranged in the Y direction. The first electrodes 30 of a column, arranged in the Y direction have the same potential.

In the ultrasonic element array 6, the ultrasonic elements 35 are arranged, and are connected to each other via the first wire 31 and the second wire 34. The first wire 31 and the second wire 34 connect the respective ultrasonic elements 35 to each other so as to be long, and thus easily receive electromagnetic noise.

The first conductive film 17 is provided on the first direction 11 side of the ultrasonic element array 6. The first conductive film 17 covers all of the ultrasonic elements 35. The first conductive film 17 substantially covers all of the first wires 31, the second wires 34, and the second sub-wires 41. Therefore, electromagnetic noise directed toward the ultrasonic element array 6 from the first direction 11 side is reflected and blocked or is absorbed and attenuated by the first conductive film 17. The first conductive film 17 can prevent electromagnetic noise from reaching the ultrasonic element array 6, the first wires 31, and the second wires 34.

First conductive film terminals 17a are formed at both ends of the first conductive film 17 on the X direction side. The first conductive film terminals 17a are adhered to the second conductive film 22 via the conductive adhesive 23. The conductive adhesive 23 is an adhesive having conductivity. Therefore, it is possible to easily perform fixation between the first conductive film 17 and the acoustic lens 12 and electrical connection between the first conductive film 17 and the second conductive film 22.

Figure 8:
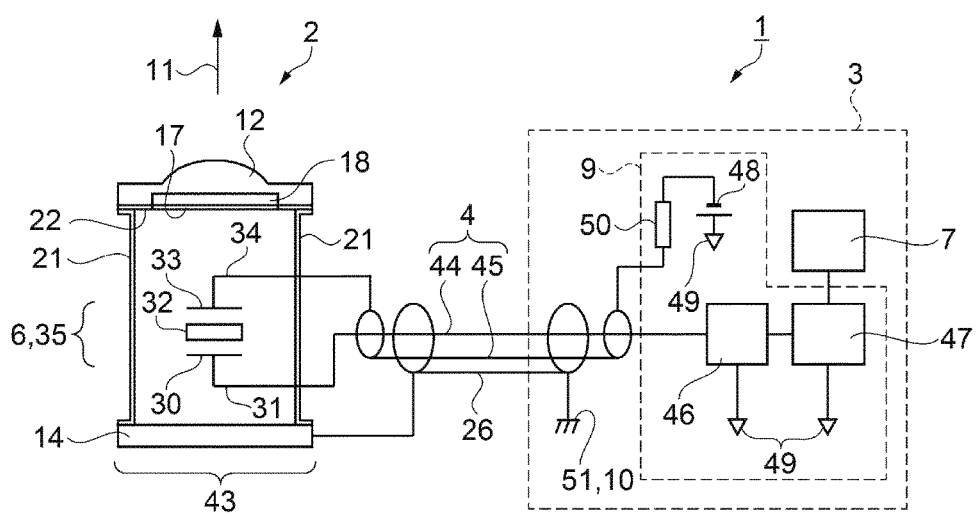
FIG. 8 is an electrical block diagram of the ultrasonic apparatus.

FIG. 8 is an electrical block diagram of the ultrasonic apparatus. A plurality of ultrasonic elements 35 are provided in the ultrasonic probe 2, but only a single ultrasonic element 35 is illustrated for better understanding of the drawing. As illustrated in FIG. 8, the ultrasonic probe 2 includes the ultrasonic element array 6 provided with the ultrasonic element 35.

The ultrasonic element array 6 is surrounded by the first conductive film 17, the second conductive film 22, the conductive member 21, and the support substrate 14. An electric wave shield portion 43 is formed by the first conductive film 17, the second conductive film 22, the conductive member 21, and the support substrate 14. Therefore, the electric wave shield portion 43 is located in the first direction 11 of the ultrasonic element array 6, the direction intersecting the first direction 11, and the direction opposite to the first direction 11. In the ultrasonic element array 6, the arranged ultrasonic elements 35 are arranged, and are connected to each other via the first wire 31 and the second wire 34. The first wire 31 and the second wire 34 connect the respective ultrasonic elements 35 to each other so as to be long, and thus easily receive electromagnetic noise.

The electric wave shield portion 43 is located in the first direction 11 of the ultrasonic element array 6, the direction intersecting the first direction 11, and the direction opposite to the first direction 11. As mentioned above, the electric wave shield portion 43 is provided to surround the ultrasonic element array 6. Therefore, electromagnetic noise directed toward the ultrasonic element array 6 from all directions is reflected and blocked or is absorbed and attenuated by the electric wave shield portion 43. As a result, the electric wave shield portion 43 can prevent the electromagnetic noise from reaching the ultrasonic element array 6.

The flat cable 4 has a structure in which a plurality of coaxial cables are arranged to be parallel to each other, and has a flat stripe shape. In the coaxial cable, an inner conductor 44 is located on an axis thereof, and an insulator, an outer conductor 45, and a protective coat are disposed in a concentric manner. The braided shield 26 covers the periphery of the flat cable 4.

In the ultrasonic probe 2, the inner conductor 44 is electrically connected to the first electrode 30 of the ultrasonic element 35. The outer conductor 45 is electrically connected to the second electrode 33 of the ultrasonic element 35. The support substrate 14 is electrically connected to the braided shield 26.

The main body portion 3 includes the calculation device 9 therein, and the calculation device 9 is provided with a transmission/reception circuit 46 and a drive circuit 47. The transmission/reception circuit 46 is electrically connected to the inner conductor 44 of the flat cable 4 and the drive circuit 47. The drive circuit 47 is electrically connected to the transmission/reception circuit 46 and the display device 7.

The transmission/reception circuit 46 transmits an electric signal to the ultrasonic element array 6, and receives an electric signal output from the ultrasonic element array 6. Specifically, the transmission/reception circuit 46 is electrically connected to the first electrode 30 of the ultrasonic element 35 via the inner conductor 44. The transmission/reception circuit 46 transmits an electric signal to the first electrode 30, and receives an electric signal output from the first electrode 30. The drive circuit 47 generates a drive signal for driving the ultrasonic element array 6. An ultrasonic image is generated by using an electric signal output from the ultrasonic element array 6, and is output to the display device 7.

The calculation device 9 includes a DC power source circuit 48, and a positive terminal of the DC power source circuit 48 is connected to a circuit ground 49 so as to be grounded. The circuit ground 49 is also electrically connected to the transmission/reception circuit 46 and the drive circuit 47. A negative terminal of the DC power source circuit 48 is connected to the outer conductor 45 of the flat cable 4 via an electrical resistor 50. The outer conductor 45 of the flat cable 4 is electrically connected to the second electrode 33. Therefore, a negative bias voltage is applied to the second electrode 33. A voltage changes centering on 0 V in the first electrode 30, and thus a voltage waveform centering on the bias voltage is applied to the piezoelectric layer 32.

In the main body portion 3, the main body casing portion 10 functions as a chassis ground 51. The braided shield 26 is electrically connected to the chassis ground 51. Since the braided shield 26 is electrically connected to the support substrate 14, the first conductive film 17, the second conductive film 22, the conductive member 21, and the support substrate 14 forming the electric wave shield portion 43 are electrically connected to the chassis ground 51 so as to be grounded to the main body casing portion 10.

As described above, according to the present embodiment, the following effects are achieved.

(1) According to the present embodiment, the ultrasonic probe 2 includes the ultrasonic element substrate 16, the casing portion 13, and the support substrate 14. The ultrasonic element substrate 16 is provided with the ultrasonic element array 6 and the first conductive film 17. The ultrasonic element array 6 transmits an ultrasonic wave in the first direction 11. In the ultrasonic element array 6, the ultrasonic elements 35 are arranged, and are connected to each other via wires. The wires connect the respective ultrasonic elements 35 to each other so as to be long, and thus easily receive electromagnetic noise.

The first conductive film 17 is provided on the first direction 11 side of the ultrasonic element array 6. Electromagnetic noise directed toward the ultrasonic element array 6 from the first direction 11 side is reflected and blocked or is absorbed and attenuated by the first conductive film 17. The casing portion 13 includes the conductive member 21, and the conductive member 21 is provided to surround the ultrasonic element substrate 16 on the side intersecting the first direction 11 of the ultrasonic element substrate 16. Therefore, electromagnetic noise directed toward the ultrasonic element array 6 from the direction side intersecting the first direction 11 is reflected and blocked or is absorbed and attenuated by the conductive member 21.

The support substrate 14 is provided on the opposite side to the first direction 11 of the ultrasonic element substrate 16, and supports the ultrasonic element substrate 16. The support substrate 14 is conductive. Therefore, electromagnetic noise which is directed toward the ultrasonic element array 6 from the opposite direction side to the first direction 11 is reflected and blocked or is absorbed and attenuated by the support substrate 14. Therefore, electromagnetic noise directed toward the ultrasonic element array 6 from all directions is reflected and blocked or is absorbed and attenuated by the first conductive film 17, the conductive member 21, and the support substrate 14, and thus it is possible to prevent the electromagnetic noise from reaching the ultrasonic element array 6.

(2) According to the present embodiment, a material of the casing portion 13 is a resin, and thus the casing portion 13 is easily formed even if a shape thereof is complex compared with a case where a material thereof is metal. The conductive member 21 is a thin film provided on the surface of the casing portion 13, and can thus be easily provided by using a film forming device such as a deposition device.

The acoustic lens 12 is provided on the first direction 11 side of the ultrasonic element substrate 16. The acoustic lens 12 protects the ultrasonic element substrate 16. The acoustic lens 12 is provided with a second conductive film 22 on the ultrasonic element substrate 16 side. The first conductive film 17, the second conductive film 22, the conductive member 21, and the support substrate 14 are electrically connected to each other. Consequently, it is possible to reduce electromagnetic noise received by the ultrasonic element array 6. The second conductive film 22 and the conductive member 21 are adhered to each other via the conductive adhesive 23. Therefore, it is possible to easily perform fixation between the acoustic lens 12 and the casing portion 13 and electrical connection between the second conductive film 22 and the conductive member 21.

(3) According to the present embodiment, a material of the first conductive film 17 is copper. The copper has low electrical resistance, and can thus absorb electromagnetic noise with high efficiency.

(4) According to the present embodiment, the ultrasonic probe 2 is provided with the flat cable 4 and the braided shield 26. The plurality of ultrasonic elements 35 are provided in the ultrasonic element array 6, and thus a plurality of wires for sending signals to the respective ultrasonic elements 35 are necessary. The wires have the form of the flat cable 4, and thus have a thin structure. Therefore, the ultrasonic probe 2 can be thinned more than in a case of using a cable in which wires are bundled in a rod shape. The braided shield 26 is provided to surround the flat cable 4. The support substrate 14 is connected to the braided shield 26. Therefore, the braided shield 26 is connected to the support substrate 14, and thus it is possible to prevent electromagnetic noise from entering the flat cable 4.

(5) According to the present embodiment, the ultrasonic probe 2 is provided with the ultrasonic element substrate 16 and the electric wave shield portion 43. The ultrasonic element substrate 16 is provided with the ultrasonic element array 6. The ultrasonic element array 6 transmits an ultrasonic wave. In the ultrasonic element array 6, the ultrasonic elements 35 are arranged, and are connected to each other via the first wire 31 and the second wire 34. The first wire 31 and the second wire 34 connect the respective ultrasonic elements 35 to each other so as to be long, and thus easily receive electromagnetic noise.

The electric wave shield portion 43 is located in the first direction 11 of the ultrasonic element array 6, the direction intersecting the first direction 11, and the direction opposite to the first direction 11. As mentioned above, the electric wave shield portion 43 is provided to surround the ultrasonic element array 6. Therefore, electromagnetic noise directed toward the ultrasonic element array 6 from all directions is reflected and blocked or is absorbed and attenuated by the electric wave shield portion 43. As a result, electromagnetic noise directed toward the ultrasonic element array 6 can be prevented from reaching the ultrasonic element array.

(6) According to the present embodiment, the ultrasonic apparatus 1 includes the ultrasonic probe 2. The ultrasonic probe 2 can prevent electromagnetic noise directed toward the ultrasonic element array 6 from reaching the ultrasonic element array. Therefore, the ultrasonic apparatus 1 can be provided as an apparatus including the ultrasonic probe 2 which can prevent electromagnetic noise directed toward the ultrasonic element array 6 from reaching the ultrasonic element array.

(7) According to the present embodiment, the first conductive film 17 is provided between the ultrasonic element substrate 16 and the acoustic lens 12. A potential of the first conductive film 17 is 0 V. In the ultrasonic element substrate 16, for example, a drive voltage of about 30 V is applied between the first electrode 30 and the second electrode 33. Even if a fracture occurs in the acoustic lens 12, the first conductive film 17 is set to be 0 V, and thus it is possible to prevent a drive voltage for driving the ultrasonic element 35 from being applied to the subject 5.

(8) According to the present embodiment, the ultrasonic element array 6 is surrounded by the electric wave shield portion 43. Therefore, the electric wave shield portion 43 can prevent electromagnetic noise generated by the ultrasonic element array 6 from being emitted from the ultrasonic probe 2. The calculation device 9 is also surrounded by the metallic main body casing portion 10. Therefore, the main body casing portion 10 reduces electromagnetic noise advancing toward the calculation device 9. The main body casing portion 10 can prevent electromagnetic noise generated by the calculation device 9 from being emitted from the main body portion 3.

Second Embodiment

Figure 9:
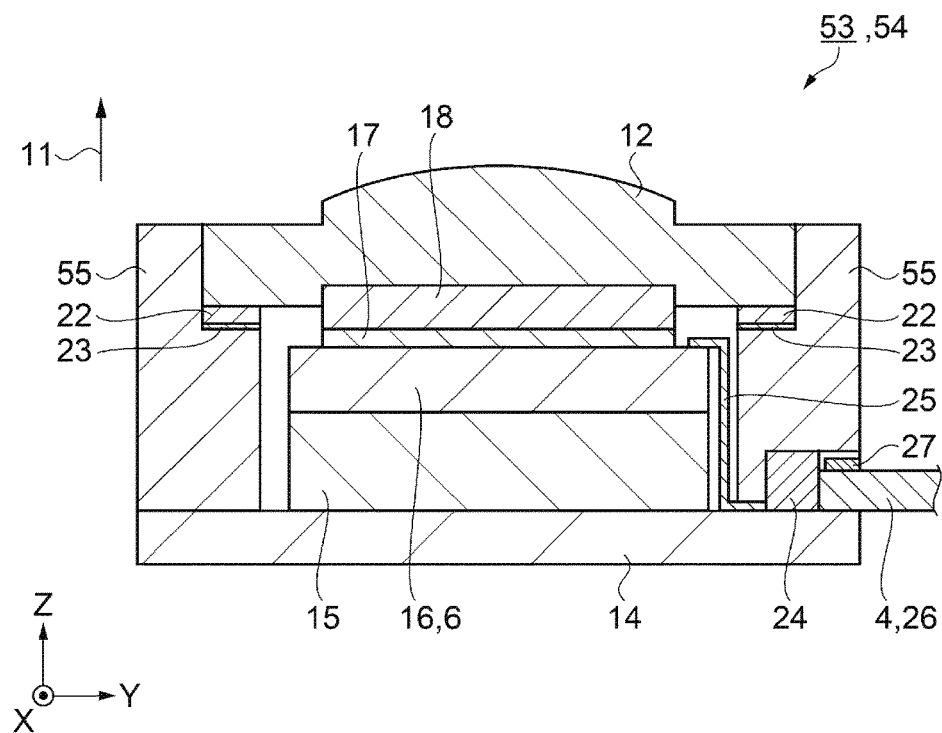
FIG. 9 is a schematic side sectional view illustrating a structure of an ultrasonic probe according to a second embodiment.
Figure 10:
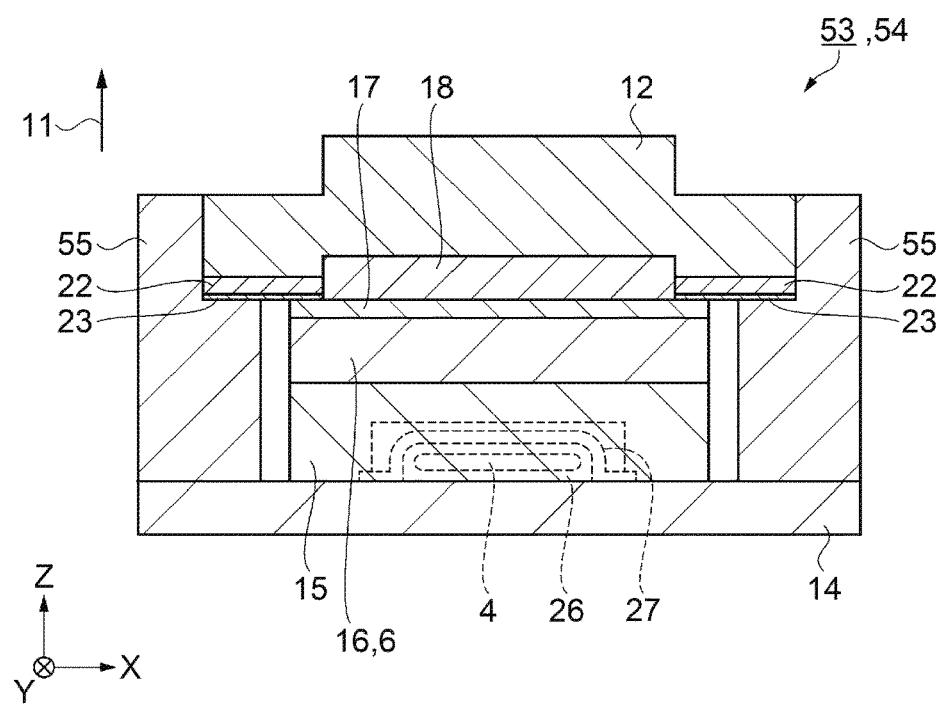
FIG. 10 is a schematic side sectional view illustrating a structure of the ultrasonic probe.

Next, an embodiment of an ultrasonic apparatus will be described with reference to schematic side sectional views illustrating a structure of an ultrasonic probe in FIGS. 9 and 10. FIG. 9 is a view in which a section is viewed from the +X direction side. FIG. 10 is a view in which a section is viewed from the −Y direction side. The present embodiment is different from the first embodiment in that a casing portion is made of a conductive material. A description of the same content as in the first embodiment will be omitted.

In other words, in the present embodiment, as illustrated in FIGS. 9 and 10, an ultrasonic probe 54 of an ultrasonic apparatus 53 includes a conductive member 55 provided on the support substrate 14. A method in which the support substrate 14 and the conductive member 55 are fixed together is not particularly limited. In the present embodiment, for example, the support substrate 14 is fixed to the conductive member 55 with screws.

A material of the conductive member 55 is not particularly limited as long as the material is conductive, but, in the present embodiment, copper is used as the material of the conductive member 55. Nickel is plated on a surface of the conductive member 55 in order to improve corrosion resistance and an external appearance thereof. As mentioned above, a shape is the same as that of the casing portion 13 in the first embodiment, and a material is the same as that of the conductive member 21 in the first embodiment. In other words, the conductive member 55 has a structure in which the conductive member 21 and the casing portion 13 in the first embodiment are integrally formed.

The conductive member 55 and the second conductive film 22 are adhered to each other via the conductive adhesive 23. Therefore, the conductive member 55 is electrically connected to the second conductive film 22. The second conductive film 22 and the first conductive film 17 are adhered to each other via the conductive adhesive 23. Therefore, the second conductive film 22 is electrically connected to the first conductive film 17. Thus, the first conductive film 17, the conductive member 55, and the support substrate 14 are electrically connected to each other.

As mentioned above, the conductive member 55 has a structure in which the conductive member 21 and the casing portion 13 in the first embodiment are integrally formed. In other words, the conductive member 55 corresponding to the casing portion 13 is made of a conductive material. The first conductive film 17, the conductive member 55, and the support substrate 14 are electrically connected to each other. In this configuration, the ultrasonic element array 6 is surrounded by the conductive member, and thus it is possible to prevent the ultrasonic element array 6 from receiving electromagnetic noise. Second processing for providing the conductive member 21 in the casing portion 13 in the first embodiment can be omitted, and thus it is possible to manufacture the ultrasonic probe 54 with high productivity.

Third Embodiment

Figure 11:
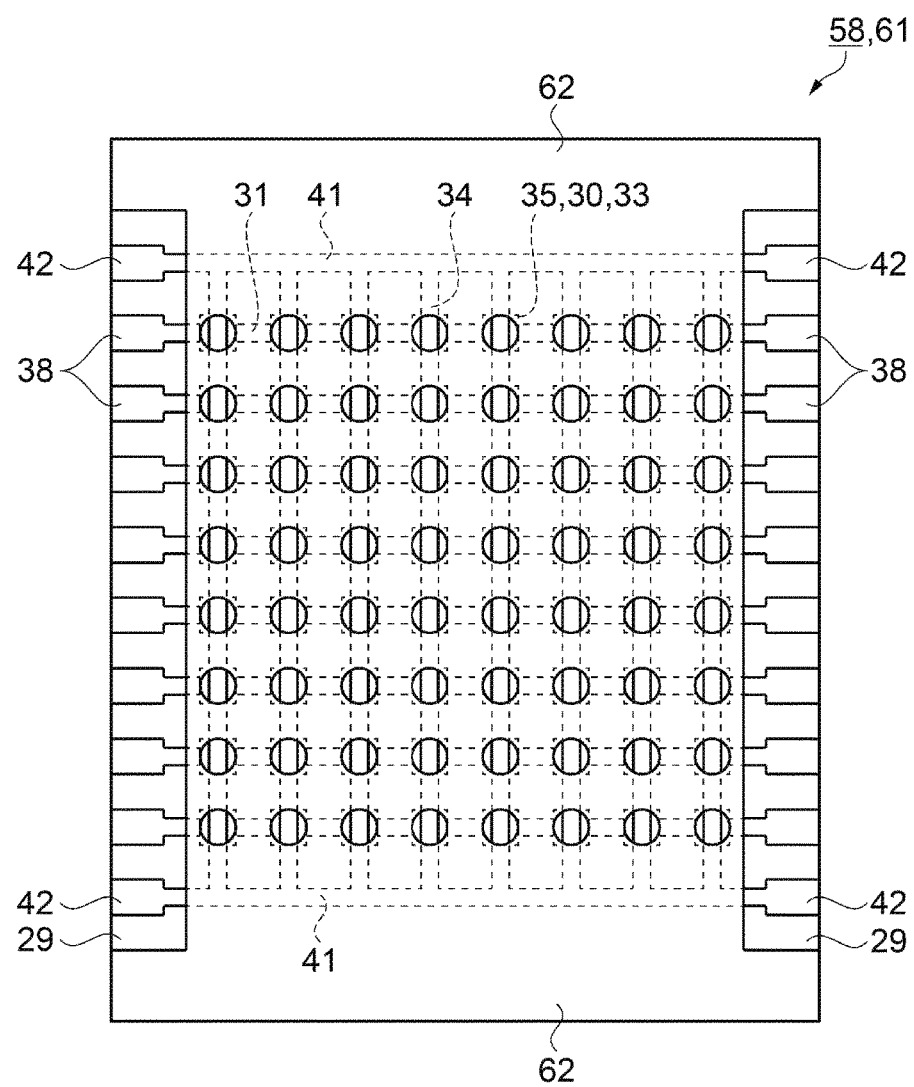
FIG. 11 is a schematic plan view illustrating a structure of an ultrasonic element array according to a third embodiment.
Figure 12:
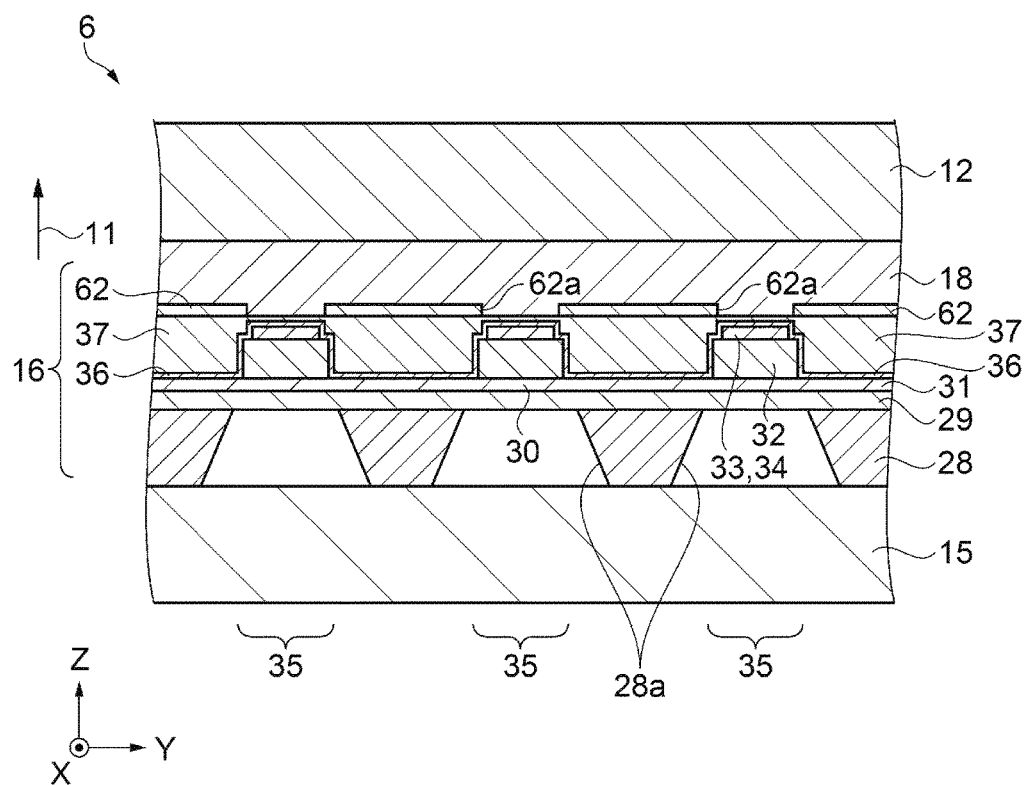
FIG. 12 is a schematic side sectional view for explaining a sectional structure of an ultrasonic element array.

Next, an embodiment of an ultrasonic apparatus will be described with reference to FIGS. 11 and 12. FIG. 11 is a schematic plan view illustrating a structure of an ultrasonic element array. FIG. 11 illustrates a state in which a first conductive film overlaps the ultrasonic element substrate 16 is viewed from the first direction 11. FIG. 12 is a schematic side sectional view for explaining of a sectional structure of an ultrasonic element array. The present embodiment is different from the first embodiment in that a plurality of holes are formed in the first conductive film 17. A description of the same content as in the first embodiment will be omitted.

In other words, in the present embodiment, as illustrated in FIGS. 11 and 12, a first conductive film 62 is provided between the internal acoustic matching portion 37 and the acoustic matching portion 18 in an ultrasonic probe 61 of an ultrasonic apparatus 58. A plurality of holes 62a are provided in the first conductive film 62. The number and positions of holes 62a are not particularly limited. The hole 62a is preferably provided at a location facing the ultrasonic element 35. An ultrasonic wave transmitted from the ultrasonic element array 6 passes through the plurality of holes 62a, and thus attenuation thereof can be reduced. Therefore, the ultrasonic probe 61 can transmit an ultrasonic wave with high efficiency.

Fourth Embodiment

Figure 13:
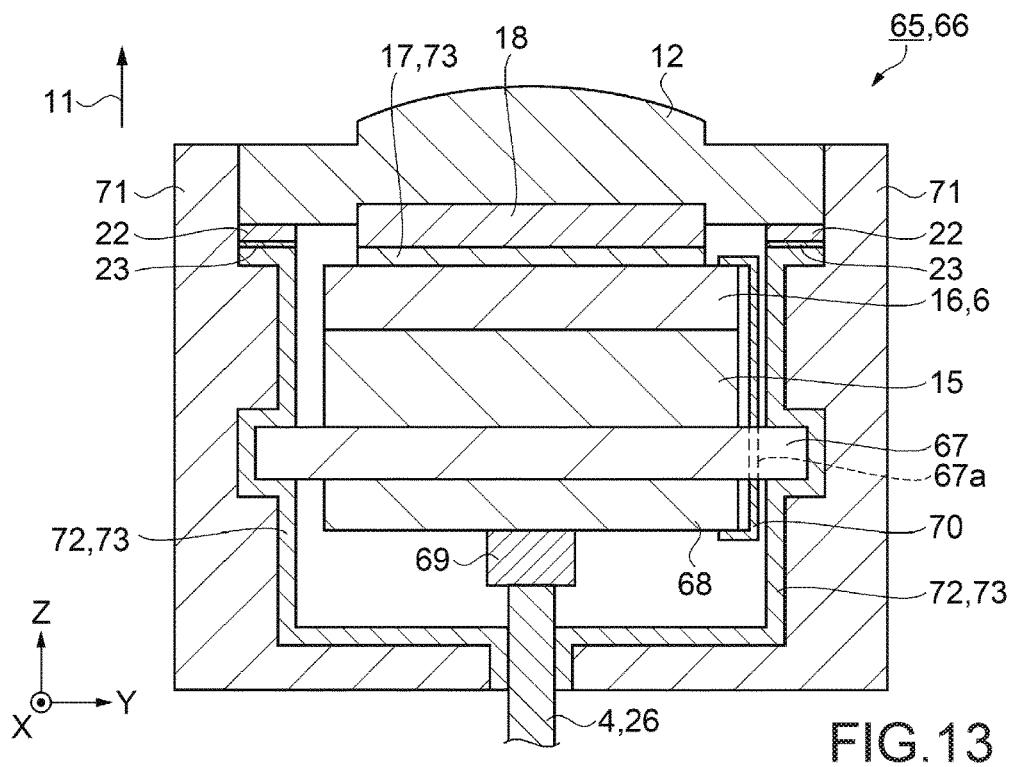
FIG. 13 is a schematic side sectional view illustrating a structure of an ultrasonic probe according to a fourth embodiment.
Figure 14:
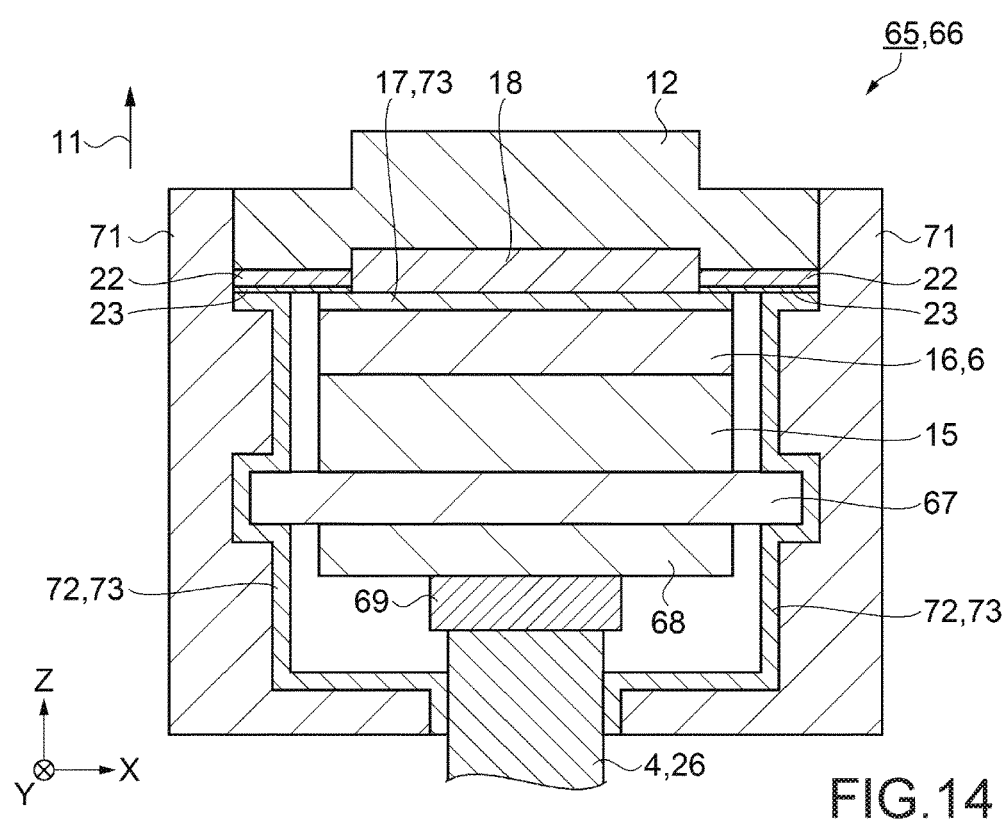
FIG. 14 is a schematic side sectional view illustrating a structure of the ultrasonic probe.

Next, an embodiment of an ultrasonic apparatus will be described with reference to schematic side sectional views illustrating a structure of an ultrasonic probe in FIGS. 13 and 14. FIG. 13 is a view in which a section is viewed from the +X direction side. FIG. 14 is a view in which a section is viewed from the −Y direction side. The present embodiment is different from the first embodiment in that the support substrate 14 is provided inside a casing portion. A description of the same content as in the first embodiment will be omitted.

As illustrated in FIGS. 13 and 14, an ultrasonic probe 66 of an ultrasonic apparatus 65 is provided with a support substrate 67. The ultrasonic wave absorption plate 15, the ultrasonic element substrate 16, the first conductive film 17, the acoustic matching portion 18, and the acoustic lens 12 are provided to overlap each other in this order on the first direction 11 side of the support substrate 67. The ultrasonic element substrate 16 is provided with the ultrasonic element array 6 transmitting ultrasonic waves in the first direction 11. The first conductive film 17 is provided on the first direction 11 side of the ultrasonic element array 6. A material of the support substrate 67 is the copper alloy as that of the support substrate 14 of the first embodiment. Therefore, the support substrate 67 is made of a conductive material.

A connector substrate 68 is provided on the −Z direction side of the support substrate 67. The connector substrate 68 is provided with a connector 69, and a circuit pattern having wires and terminals (not illustrated) is provided on the connector substrate 68. The terminals on the connector substrate 68 are electrically connected to the first terminals 38 and the second terminals 42 on the ultrasonic element substrate 16 via a flexible printed wiring board 70. The support substrate 67 is provided with a through-hole 67a on the +Y direction side. The flexible printed wiring board 70 is disposed through the through-hole 67a.

The connector 69 is connected to the flat cable 4. The braided shield 26 is provided to cover the periphery of the flat cable 4.

A rectangular cylindrical casing portion 71 is provided on the Y direction side and the X direction side of the connector substrate 68, the support substrate 67, the ultrasonic wave absorption plate 15, the ultrasonic element substrate 16, the first conductive film 17, the acoustic matching portion 18, and the acoustic lens 12. In this configuration, the casing portion 71 is provided to surround the ultrasonic element substrate 16 on aside intersecting the first direction 11 of the ultrasonic element substrate 16. The casing portion 71 is also provided to surround the ultrasonic element substrate 16 on the opposite side to the first direction 11 with respect to the ultrasonic element substrate 16. A conductive member 72 is provided inside the casing portion 71.

As a material of the conductive member 72, metal or the like may be used in the same manner as in the first embodiment. In the present embodiment, for example, copper is used as the material of the conductive member 72.

The first wire 31 and the second wire 34 are provided in the ultrasonic element array 6, and thus easily receive electromagnetic noise. The first conductive film 17 is provided on the first direction 11 side of the ultrasonic element substrate 16 provided with the ultrasonic element array 6. Electromagnetic noise directed toward the ultrasonic element array 6 from the first direction 11 side is reflected and blocked or is absorbed and attenuated by the first conductive film 17. The casing portion 71 includes the conductive member 72, and the conductive member 72 is provided to on the side intersecting the first direction 11 and the opposite side to the first direction 11 of the ultrasonic element substrate 16. Therefore, electromagnetic noise directed toward the ultrasonic element array 6 from the direction side intersecting the first direction 11 and the opposite side to the first direction 11 is reflected and blocked or is absorbed and attenuated by the conductive member 72. Therefore, electromagnetic noise directed toward the ultrasonic element array 6 from all directions is reflected and blocked or is absorbed and attenuated by the first conductive film 17 and the conductive member 72, and thus it is possible to reduce the electromagnetic noise directed toward the ultrasonic element array 6.

An electric wave shield portion 73 is formed by the first conductive film 17 and the conductive member 72. The electric wave shield portion 73 is made of a conductive material, and is disposed to surround the ultrasonic element substrate 16 provided with the ultrasonic element array 6.

The electric wave shield portion 73 is located in the first direction 11 of the ultrasonic element array 6, the direction intersecting the first direction 11, and the direction opposite to the first direction 11. As mentioned above, the electric wave shield portion 73 is provided to surround the ultrasonic element array 6. Therefore, electromagnetic noise directed toward the ultrasonic element array 6 from all directions is reflected and blocked or is absorbed and attenuated by the electric wave shield portion 73. As a result, it is possible to prevent the electromagnetic noise from reaching the ultrasonic element array.

Fifth Embodiment

Next, an embodiment of an ultrasonic apparatus will be described with reference to an electrical block diagram of an ultrasonic apparatus in FIG. 15. A plurality of ultrasonic elements 35 are provided in the ultrasonic probe 2, but only a single ultrasonic element 35 is illustrated for better understanding of the drawing. The present embodiment is different from the first embodiment in terms of a method of applying a bias voltage of an electric signal applied to the ultrasonic element 35. A description of the same content as in the first embodiment will be omitted.

Figure 15:
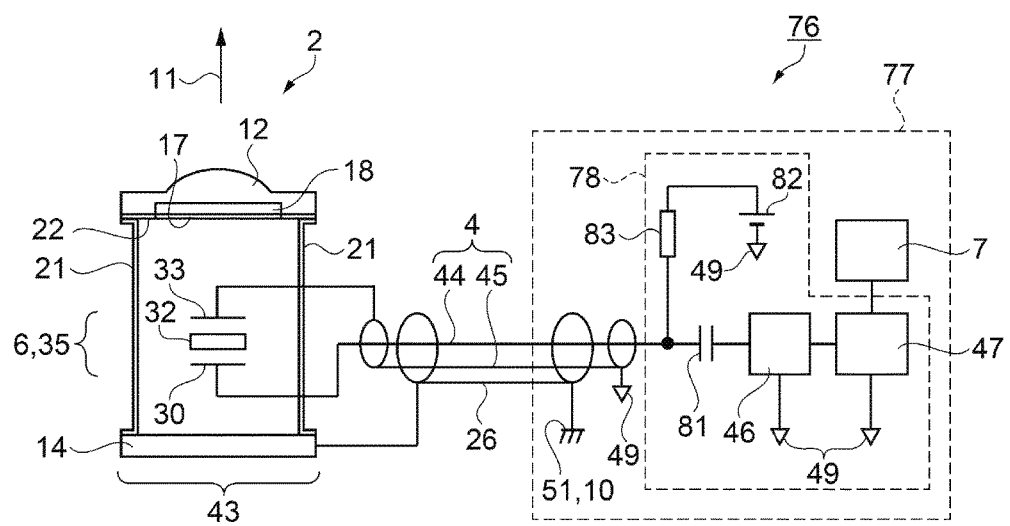
FIG. 15 is an electrical block diagram of an ultrasonic apparatus according to a fifth embodiment.

FIG. 15 is an electrical block diagram of an ultrasonic apparatus. As illustrated in FIG. 15, an ultrasonic apparatus 76 includes a main body portion 77 and an ultrasonic probe 2. The ultrasonic probe 2 includes the ultrasonic element array 6 provided with the ultrasonic element 35. The main body portion 77 includes a calculation device 78 therein, and the calculation device 78 is provided with a transmission/reception circuit 46 and a drive circuit 47. The transmission/reception circuit 46 is electrically connected to the inner conductor 44 of the flat cable 4 and the drive circuit 47. The drive circuit 47 is electrically connected to the transmission/reception circuit 46 and the display device 7.

Specifically, the transmission/reception circuit 46 is connected to a capacitor 81, and the capacitor 81 is connected to the inner conductor 44 of the flat cable 4. The capacitor 81 is provided to cause only an AC component to pass therethrough. The inner conductor 44 is electrically connected to the first electrode 30 of the ultrasonic element 35.

The calculation device 78 includes a DC power source circuit 82, and a negative terminal of the DC power source circuit 82 is connected to a circuit ground 49 so as to be grounded. The circuit ground 49 is also electrically connected to the transmission/reception circuit 46 and the drive circuit 47. A positive terminal of the DC power source circuit 82 is connected to the inner conductor 44 of the flat cable 4 via an electrical resistor 83. A positive bias voltage is applied to the first electrode 30. A voltage applied to the first electrode 30 changes centering on the positive bias voltage.

The outer conductor 45 of the flat cable 4 is connected to the circuit ground 49. The outer conductor 45 of the flat cable 4 is electrically connected to the second electrode 33. Therefore, a voltage of the second electrode 33 is 0 V. A voltage changes centering on the positive bias voltage in the first electrode 30, and thus a voltage waveform centering on the positive bias voltage is applied to the piezoelectric layer 32.

As mentioned above, a voltage waveform for driving the ultrasonic element 35 is different from that in the first embodiment. Also in this case, the electric wave shield portion 43 can reduce electromagnetic noise directed toward the ultrasonic element array 6. Since the support substrate 14 is electrically connected to the chassis ground 51, it is possible to further reduce electromagnetic noise reaching the ultrasonic element array.

Sixth Embodiment

Next, an embodiment of an ultrasonic apparatus will be described with reference to a schematic side sectional view illustrating a structure of an ultrasonic probe in FIG. 16. The present embodiment is different from the first embodiment in that the acoustic lens 12 having a convex lens is replaced with a flat protective member. A description of the same content as in the first embodiment will be omitted.

Figure 16:
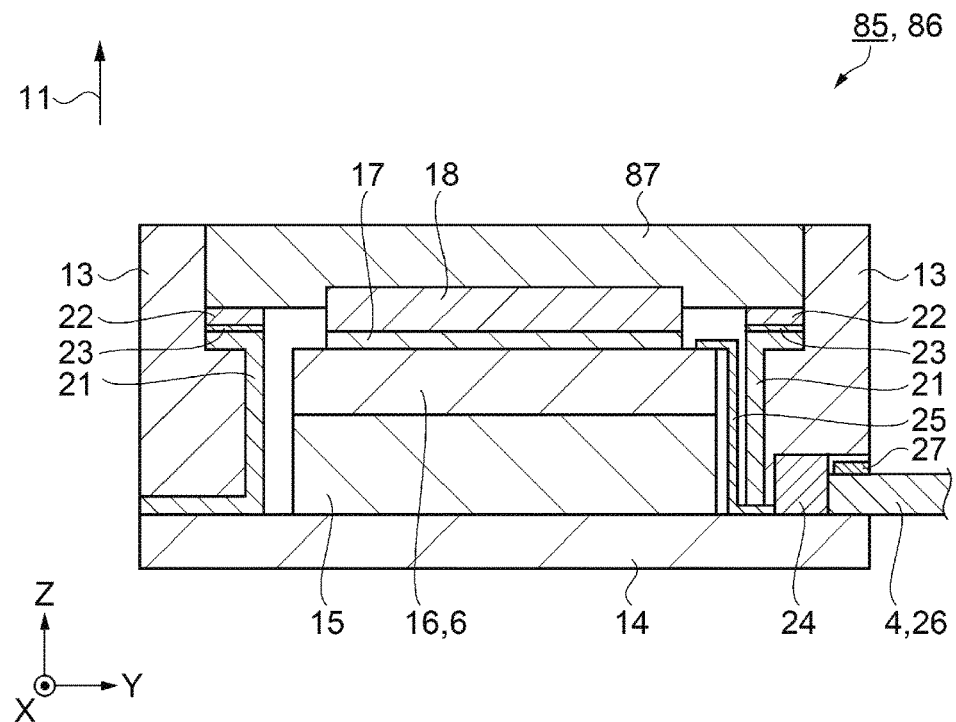
FIG. 16 is a schematic side sectional view illustrating a structure of an ultrasonic probe according to a sixth embodiment.

In other words, as illustrated in FIG. 16, in an ultrasonic probe 86 of an ultrasonic apparatus 85, the first conductive film 17, the acoustic matching portion 18, and a protective member 87 are provided to overlap each other in this order on the first direction 11 side of the ultrasonic element substrate 16. A surface of the protective member 87 on the first direction 11 side is flat. Ultrasonic waves transmitted from the ultrasonic element substrate 16 are not collected at the protective member 87 and advance in the first direction 11.

The ultrasonic probe 86 can transmit ultrasonic waves faraway. The ultrasonic probe 86 can receive a reflected wave of an ultrasonic wave which is transmitted therefrom toward the air and is reflected at a remote location. Also in the ultrasonic probe 86, the first conductive film 17, the second conductive film 22, the conductive member 21, and the support substrate 14 surround the ultrasonic element array 6. Therefore, it is possible to prevent electromagnetic noise from reaching the ultrasonic element array 6.

Seventh Embodiment

Next, an embodiment of an ultrasonic apparatus will be described with reference to a schematic side sectional view illustrating a structure of an ultrasonic probe in FIG. 17. The present embodiment is different from the first embodiment in that the acoustic lens 12 is omitted, and the first conductive film 17 and the casing portion 13 are integrally formed. A description of the same content as in the first embodiment will be omitted.

Figure 17:
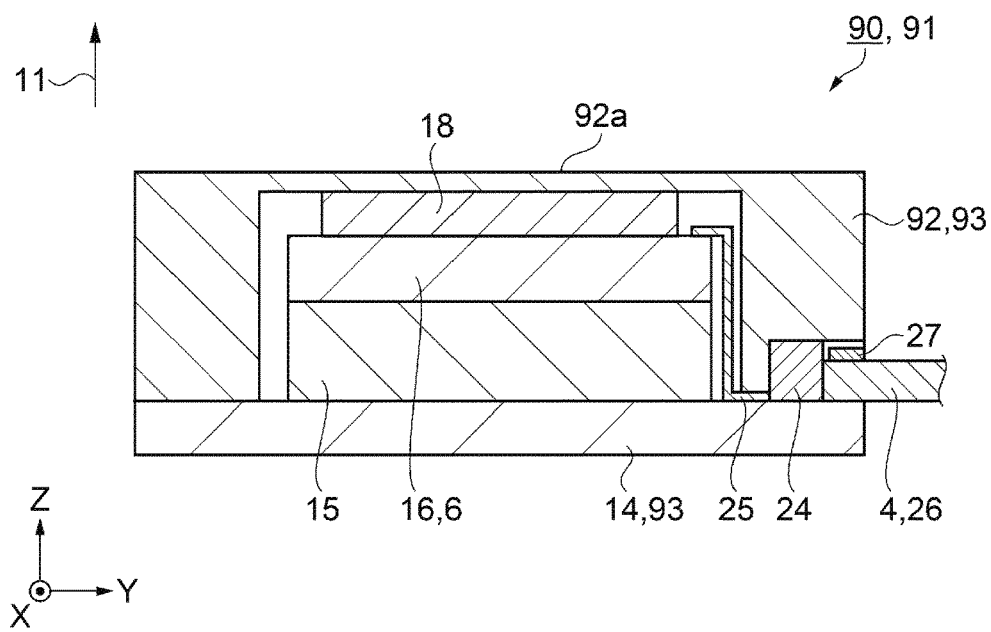
FIG. 17 is a schematic side sectional view illustrating a structure of an ultrasonic probe according to a seventh embodiment.

In other words, as illustrated in FIG. 17, in an ultrasonic probe 91 of an ultrasonic apparatus 90, the ultrasonic wave absorption plate 15, the ultrasonic element substrate 16, and the acoustic matching portion 18 are provided to overlap each other in this order on the first direction 11 side of the support substrate 14. A bottomed rectangular cylindrical casing portion 92 is provided on the first direction 11 side of the support substrate 14. A material of the casing portion 92 is the same conductor as that of the conductive member 21 in the first embodiment. Specifically, a material of the casing portion 92 is copper or a copper alloy, and a nickel film is formed on a surface of the casing portion 92 through nickel plating.

The casing portion 92 has a form of a conductive film 92a corresponding to the first conductive film 17 on the first direction 11 side. The conductive film 92a is in close contact with the acoustic matching portion 18. An electric wave shield portion 93 is formed by the support substrate 14 and the casing portion 92.

The electric wave shield portion 93 is located in the first direction 11 of the ultrasonic element array 6, the direction intersecting the first direction 11, and the direction opposite to the first direction 11. As mentioned above, the electric wave shield portion 93 is provided to surround the ultrasonic element array 6. Therefore, electromagnetic noise directed toward the ultrasonic element array 6 from all directions is reflected and blocked or is absorbed and attenuated by the electric wave shield portion 93. As a result, it is possible to prevent the electromagnetic noise from reaching the ultrasonic element array 6.

According to the present embodiment, the ultrasonic probe 91 has a structure in which the first conductive film 17, the conductive member 21, and the casing portion 13 in the first embodiment are integrally formed. In other words, the casing portion 92 is made of a conductive material. The casing portion 92 is electrically connected to the support substrate 14. In this configuration, the ultrasonic element array 6 is surrounded by the conductive member, and thus it is possible to prevent the ultrasonic element array 6 from receiving electromagnetic noise. In the casing portion 92, second processing for providing the conductive member 21 in the casing portion 13 in the first embodiment can be omitted, and thus it is possible to manufacture the ultrasonic probe 91 with high productivity.

The present embodiment is not limited to the above-described embodiments, and may be variously modified or altered by a person skilled in the art within the technical spirit of the invention. Modification examples will now be described.

Modification Example 1

In the first embodiment, the conductive member 21 is provided by using a film forming device such as a deposition device. Conductive particles such as metal may be dispersed into an adhesive, and may be applied. A metal component may be subjected to insert molding. The ultrasonic probe 2 can be manufactured with high productivity by selecting an easy manufacturing method.

Modification Example 2

In the first embodiment, the ultrasonic element array 6 is provided on the ultrasonic element substrate 16. A single ultrasonic element 35 may be provided on the ultrasonic element substrate 16. Also in this case, the electric wave shield portion 43 can prevent electromagnetic noise from reaching the ultrasonic element 35.

Modification Example 3

In the second embodiment, copper is used as a material of the conductive member 55, and nickel is plated on the surface of the conductive member 55. Aluminum may be used as a material of the conductive member 55, and alumite treatment may be performed on the surface of the conductive member 55.

In the seventh embodiment, copper is used as a material of the casing portion 92, and nickel is plated on the surface of the casing portion 92. Aluminum may be used as a material of the casing portion 92, and alumite treatment may be performed on the surface of the casing portion 92. The aluminum also has conductivity in the same manner as the copper, and reflects and blocks or absorbs and attenuates electromagnetic noise. Since the aluminum is easier to obtain than the copper, materials can be easily procured.

Modification Example 4

In the first embodiment, a description has been made of an example of the ultrasonic probe 2 which transmits an ultrasonic wave to the subject 5. The structure of the electric wave shield portion may be used for an ultrasonic apparatus which detects the presence or absence of an object to be measured by using an ultrasonic wave. The structure of the electric wave shield portion may be used for an ultrasonic apparatus which measures a distance between an object to be measured and the ultrasonic apparatus by using an ultrasonic wave. Also in this case, it is possible to prevent electromagnetic noise from reaching the ultrasonic element 35.

The entire disclosure of Japanese Patent Application No. 2017-150475, filed Aug. 3, 2017 is expressly incorporated by reference herein.

What is claimed is:

1. An ultrasonic apparatus comprising:
   an ultrasonic element substrate including an ultrasonic element array, the ultrasonic element array transmitting an ultrasonic wave in a first direction;
   a first conductive film provided on a first side of the ultrasonic element substrate in the first direction;
   a protective member provided at the first side of the ultrasonic element substrate;
   a second conductive member provided at a periphery of the protective member on a bottom surface of the protective member, the bottom surface facing the ultrasonic element substrate;
   a case having a conductive member, the conductive member laterally surrounding a side of the ultrasonic element substrate in a second direction intersecting the first direction, the conductive member being a thin film provided on a surface of the case, the case being made of a material having a resin; and
   a support substrate that is provided on a second side opposite to the first side in the first direction of the ultrasonic element substrate, the support substrate supporting the ultrasonic element substrate, the support substrate having conductivity,
   wherein the first conductive film, the second conductive film, the conductive member, and the support substrate are electrically connected to each other, and
   the second conductive film is adhered to the conductive member via a conductive adhesive.

2. The ultrasonic apparatus according to claim 1, wherein the conductive member and the case are integrally formed with each other.

3. The ultrasonic apparatus according to claim 1, wherein a material of the first conductive film is copper.

4. The ultrasonic apparatus according to claim 1, wherein the first conductive film is provided with a plurality of holes.

5. The ultrasonic apparatus according to claim 1, further comprising:
   a flat cable through which an electric signal is transmitted to the ultrasonic element array; and a braided shield that surrounds the flat cable,
wherein the support substrate is connected to the braided shield.

6. An ultrasonic apparatus comprising:
an ultrasonic element substrate including an ultrasonic element array, the ultrasonic element array transmitting an ultrasonic wave in a first direction;
a first conductive film provided on a first side of the ultrasonic element substrate in the first direction;
a second conductive member provided at a periphery of the protective member on a bottom surface of the protective member, the bottom surface facing the ultrasonic element substrate,
a case having a conductive member, the conductive member laterally surrounding a side of the ultrasonic element substrate in a second direction intersecting the first direction, the conductive member being a thin film provided on a surface of the base, the case being made of a material having a resin;
a support substrate that is provided on a second side opposite to the first side in the first direction of the ultrasonic element substrate, the support substrate supporting the ultrasonic element substrate, the support substrate having conductivity; and
an electric wave shield for the ultrasonic apparatus is configured with the first conductive film, the second conductive film, the conductive member, and the support substrate to enclose the ultrasonic element array,
wherein the first conductive film, the second conductive film, the conductive member, and the support substrate are electrically connected to each other, and
the second conductive film is adhered to the conductive member via a conductive adhesive.

7. The ultrasonic apparatus according to claim 6,
wherein the conductive member and the case are integrally formed with each other.

8. The ultrasonic apparatus according to claim 6,
wherein a material of the first conductive film is copper.

9. The ultrasonic apparatus according to claim 6,
wherein the first conductive film is provided with a plurality of holes.

10. The ultrasonic apparatus according to claim 6, further comprising:
a flat cable through which an electric signal is transmitted to the ultrasonic element array; and
a braided shield that surrounds the flat cable,
wherein the support substrate is connected to the braided shield.

11. An ultrasonic apparatus comprising:
an ultrasonic element substrate including an ultrasonic element array, the ultrasonic element array transmitting an ultrasonic wave in a first direction;
a first conductive film provided on a first side of the ultrasonic element substrate in the first direction;
a protective member provided at the first side of the ultrasonic element substrate;
a second conductive member provided at a periphery of the protective member on a bottom surface of the protective member, the bottom surface facing the ultrasonic element substrate;
a case having a conductive member, the conductive member laterally surrounding a side of the ultrasonic element substrate in a second direction intersecting the first direction, the conductive member being disposed at a second side opposite to the first side in the first direction of the ultrasonic element substrate; and
a support substrate that is provided on the second side of the ultrasonic element substrate, the support substrate support the ultrasonic element substrate, the support substrate having conductivity,
wherein the first conductive film, the second conductive film, the conductive member, and the support substrate are electrically connected to each other, and
the second conductive film is adhered to the conductive member via a conductive adhesive.

12. The ultrasonic apparatus according to claim 11,
wherein the conductive member and the case are integrally formed.

13. The ultrasonic apparatus according to claim 11,
wherein a material of the first conductive film is copper.

14. The ultrasonic apparatus according to claim 11,
wherein the first conductive film is provided with a plurality of holes.

15. The ultrasonic apparatus according to claim 11, further comprising:
a flat cable through which an electric signal is transmitted to the ultrasonic element array; and
a braided shield that surrounds the flat cable,
wherein the support substrate is connected to the braided shield.

* * * * *